(12) United States Patent
Jung et al.

(10) Patent No.: US 10,383,593 B2
(45) Date of Patent: Aug. 20, 2019

(54) METHOD AND APPARATUS FOR PHOTOGRAPHING MEDICAL IMAGE

(71) Applicant: SAMSUNG ELECTRONICS CO., LTD., Suwon-si (KR)

(72) Inventors: Ji-young Jung, Bucheon-si (KR); Toshihiro Rifu, Suwon-si (KR); Chang-lae Lee, Suwon-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 370 days.

(21) Appl. No.: 15/150,866

(22) Filed: May 10, 2016

(65) Prior Publication Data

US 2016/0345928 A1    Dec. 1, 2016

(30) Foreign Application Priority Data

May 27, 2015    (KR) .................. 10-2015-0073921

(51) Int. Cl.
    *A61B 6/00*    (2006.01)
    *A61B 6/03*    (2006.01)
    *A61B 6/10*    (2006.01)

(52) U.S. Cl.
CPC .............. *A61B 6/542* (2013.01); *A61B 6/032* (2013.01); *A61B 6/107* (2013.01); *A61B 6/4405* (2013.01); *A61B 6/4464* (2013.01); *A61B 6/461* (2013.01)

(58) Field of Classification Search
CPC .... A61N 2005/1056; A61N 2005/1094; A61N 5/1031; A61N 5/103; A61N 5/1042; A61N 5/1048; A61B 6/107; A61B 6/461; A61B 6/542
See application file for complete search history.

(56) References Cited

U.S. PATENT DOCUMENTS 5,570,403 A  * 10/1996 Yamazaki .............. A61B 6/032
                                                              378/19
6,983,230 B2 *  1/2006 Baroudi ................ A61L 2/0011
                                                             434/218
(Continued)

FOREIGN PATENT DOCUMENTS

JP        2001281340 A    10/2001
JP          3449561 B2     9/2003
(Continued)

OTHER PUBLICATIONS

Communication dated Sep. 12, 2016, issued by the International Searching Authority in counterpart International Application No. PCT/KR2016/004841 (PCT/ISA/210 & PCT/ISA/237).

(Continued)

*Primary Examiner* — David J Makiya
*Assistant Examiner* — Soorena Kefayati
(74) *Attorney, Agent, or Firm* — Sughrue Mion, PLLC

(57) ABSTRACT

A tomography apparatus includes: an X-ray generator which emits X-rays; a controller which determines a first value based on a threshold dosage of the X-rays allowed for a subject and generates an absorbed-dose distribution diagram which indicates a location range of the subject in which, when the X-rays are irradiated to the subject based on an imaging condition, an absorbed dose of the X-ray has the first value; and an indicator showing the absorbed-dose distribution diagram.

28 Claims, 17 Drawing Sheets

(56) References Cited

U.S. PATENT DOCUMENTS

| | | | | |
|---|---|---|---|---|
| 7,110,495 | B2* | 9/2006 | Tamegai | A61B 6/00 378/108 |
| 7,119,903 | B1* | 10/2006 | Jones | G01N 21/47 356/446 |
| 7,471,759 | B2* | 12/2008 | Rinkel | A61B 6/5282 378/18 |
| 8,238,516 | B2 | 8/2012 | Sakurai et al. | |
| 8,552,858 | B2 | 10/2013 | Hohmann et al. | |
| 9,025,724 | B2 | 5/2015 | Lee | |
| 9,486,647 | B2* | 11/2016 | Bergfjord | A61N 5/1048 |
| 2004/0017890 | A1* | 1/2004 | Arenson | A61B 6/107 378/95 |
| 2009/0010390 | A1* | 1/2009 | Saoudi | A61N 5/1048 378/97 |
| 2009/0175418 | A1* | 7/2009 | Sakurai | A61N 5/1048 378/98.5 |
| 2010/0127859 | A1* | 5/2010 | Hohmann | A61N 5/1048 340/540 |
| 2012/0213326 | A1* | 8/2012 | Walker | A61B 6/032 378/4 |
| 2012/0314842 | A1* | 12/2012 | Kargar | A61B 6/107 378/86 |
| 2014/0348306 | A1* | 11/2014 | Van Der Veen | A61B 6/583 378/207 |
| 2015/0043712 | A1 | 2/2015 | Wang et al. | |
| 2015/0100290 | A1* | 4/2015 | Falt | A61N 5/1075 703/2 |
| 2016/0114187 | A1* | 4/2016 | Ishii | A61N 5/1038 378/42 |

FOREIGN PATENT DOCUMENTS

| | | |
|---|---|---|
| JP | 200465815 A | 3/2004 |
| JP | 2009160308 A | 7/2009 |
| KR | 101179540 B1 | 9/2012 |
| WO | 2008104915 A2 | 9/2008 |
| WO | 2015044016 A1 | 4/2015 |

OTHER PUBLICATIONS

Communication dated Oct. 11, 2016, issued by the European Patent Office in counterpart European Application No. 16171532.1.

* cited by examiner

METHOD AND APPARATUS FOR PHOTOGRAPHING MEDICAL IMAGE

CROSS-REFERENCE TO RELATED APPLICATION

This application claims priority from Korean Patent Application No. 10-2015-0073921, filed on May 27, 2015, in the Korean Intellectual Property Office, the disclosure of which is incorporated herein by reference in its entirety.

BACKGROUND

1. Field

One or more exemplary embodiments relate to a method and apparatus for capturing a medical image, and more particularly, to a method and apparatus for capturing a medical image, which enables a quick judgment to be made as to whether a subject is sufficiently far away from the apparatus for capturing a medical image for safety purposes.

2. Description of the Related Art

Apparatuses for capturing a medical image are electronic devices which may generate and process a variety of medical images. In detail, apparatuses for capturing a medical image obtain an image of an internal structure of an object. The apparatuses for capturing a medical image enable users to view an image of the object after capturing and processing an image of structural details of a body, internal organs, and flow of body fluids. Users, including doctors, may diagnose medical conditions and diseases of a patient by using the medical image generated by apparatuses for capturing a medical image.

Among apparatuses for capturing the medical image, examples of the apparatuses which acquire medical images by using X-rays may include an X-ray apparatus and a computed tomography (CT) imaging apparatus.

In order to obtain medical images by using X-rays, apparatuses for capturing a medical image irradiate X-rays to a human body. X-ray radiation is a type of high energy radiation which is harmful to the human body. Therefore, there is a need to minimize the degree of X-ray radiation that is exposed to users such as a doctor, a nurse or a radiographer, who operates the apparatuses for capturing a medical image for obtaining the medical image by using X-rays.

The dose of X-ray radiation, which is emitted from a point of X-ray irradiation to the user, decreases as it gets farther away from the point of X-ray irradiation. Therefore, the user may stay as far away as he/she feels safe from the point of X-ray irradiation, in order to minimize the degree to which he/she is exposed to X-ray radiation, when not using the apparatus for capturing a medical image.

However, it is not easy for the user to recognize the degree to which he/she is exposed to X-ray radiation while using the apparatus for capturing a medical image. In addition, it is not easy for the user to recognize whether he/she is as far away as necessary to be safe from the medical image apparatus.

In detail, when the user uses a portable apparatus for capturing a medical image, it is much more difficult for the user to recognize whether he/she is as far away as possible to be safe from the apparatus for capturing a medical image, if the place, where the apparatus for capturing a medical image is used, is changed.

SUMMARY

One or more exemplary embodiments include a method and apparatus for capturing a medical image, which facilitates a quick judgment as to whether a subject is as far away from the apparatus for capturing a medical image as necessary for safety purposes.

Additional aspects will be set forth in part in the description which follows and, in part, will be apparent from the description, or may be learned by practice of the presented exemplary embodiments.

According to one or more exemplary embodiments, a tomography apparatus may include an X-ray generator configured to emit at least one X-ray; a controller configured to determine a first value based on a threshold dosage of the at least one X-ray allowed for a subject and to generate an absorbed-dose distribution diagram that indicates a location range of the subject in which, when the at least one X-ray is irradiated to the subject based on an imaging condition, an absorbed dose of the at least one X-ray has the first value; and an indicator configured to show the generated absorbed-dose distribution diagram.

According to one or more exemplary embodiments, the absorbed-dose distribution diagram of the tomography apparatus may include a curve which indicates the location range.

According to one or more exemplary embodiments, the indicator of the tomography apparatus may include a laser beam radiator configured to show, by using a laser beam, the absorbed-dose distribution diagram on a plane on which the tomography apparatus is located.

According to one or more exemplary embodiments, the indicator of the tomography apparatus may include a display that is wirelessly connected to the controller, and the display may be configured to display the absorbed-dose distribution diagram on a screen of the display.

According to one or more exemplary embodiments, the controller of the tomography apparatus may be further configured to determine respective first values for a plurality of subjects, based on respective threshold dosages of the at least one X-ray allowed for the plurality of subjects.

According to one or more exemplary embodiments, the absorbed-dose distribution diagram shown by the indicator may include a plurality of curves that indicate respective location ranges of the plurality of subjects which correspond to the respective first values of the plurality of subjects.

According to one or more exemplary embodiments, the plurality of subjects of the tomography apparatus may include at least one from among a radiology technician and a user who wears a lead apron.

According to one or more exemplary embodiments, the controller of the tomography apparatus may be further configured to update the absorbed-dose distribution diagram based on the imaging condition, when the imaging condition changes.

According to one or more exemplary embodiments, the controller of the tomography apparatus may be further configured to update the absorbed-dose distribution diagram based on a location of a radiation shield that has been detected and a shielding rate of the detected radiation shield.

According to one or more exemplary embodiments, the radiation shield of the tomography apparatus may be detectable, by using a camera attached to the subject.

According to one or more exemplary embodiments, the imaging condition of the tomography apparatus may include at least one from among a tube voltage of the at least one X-ray, a tube current of the at least one X-ray, an irradiation duration of the at least one X-ray, and a beam width of the at least one X-ray.

According to one or more exemplary embodiments, the absorbed-dose distribution diagram shown by the indicator may indicate at least a portion of the location range, based on a current location of the subject.

According to one or more exemplary embodiments, the absorbed-dose distribution diagram shown by the indicator may be updated, based on a movement of the tomography apparatus.

According to one or more exemplary embodiments, the tomography apparatus may include a portable computer tomography (CT) apparatus.

According to one or more exemplary embodiments, an X-ray apparatus may include an X-ray radiator configured to emit at least one X-ray; a controller configured to determine a first value based on a threshold dosage of the at least one X-ray allowed for the subject and to generate an absorbed-dose distribution diagram which indicates a location range of the subject in which, when the at least one X-ray is irradiated to the subject based on an imaging condition, an absorbed dose of the at least one X-ray has the first value; and an indicator configured to show the generated absorbed-dose distribution diagram.

According to one or more exemplary embodiments, the absorbed-dose distribution diagram of the X-ray apparatus may include a curve that indicates the location range.

According to one or more exemplary embodiments, the indicator of the X-ray apparatus may include a laser beam radiator configured to show, by using a laser beam, the absorbed-dose distribution diagram on a plane on which the X-ray apparatus is located.

According to one or more exemplary embodiments, the indicator of the X-ray apparatus may include a display that is wirelessly connected to the controller, and the display may be configured to display the absorbed-dose distribution diagram on a screen of the display.

According to one or more exemplary embodiments, the controller of the X-ray apparatus may be further configured to determine respective first values for each of a plurality of subjects, based on respective threshold dosages of the at least one X-ray allowed for the plurality of subjects.

According to one or more exemplary embodiments, the absorbed-dose distribution diagram shown by the indicator may include a plurality of curves that indicate respective location ranges of the plurality of subjects which correspond to the respective first values of the plurality of subjects.

According to one or more exemplary embodiments, the plurality of subjects of the X-ray apparatus may include at least one from among a radiology technician and a user who wears a lead apron.

According to one or more exemplary embodiments, the controller of the X-ray apparatus may be further configured to update the absorbed-dose distribution diagram based on the imaging condition when the imaging condition changes.

According to one or more exemplary embodiments, the controller of the X-ray apparatus may be further configured to update the absorbed-dose distribution diagram based on a location of a radiation shield that has been detected and a shielding rate of the radiation shield.

According to one or more exemplary embodiments, the radiation shield of the X-ray apparatus may be detectable, by using a camera attached to the subject.

According to one or more exemplary embodiments, the imaging condition of the X-ray apparatus may include at least one from among the tube voltage of the at least one X-ray, the tube current of the at least one X-ray, the irradiation duration of the at least one X-ray, and the beam width of the at least one X-ray.

According to one or more exemplary embodiments, the absorbed-dose distribution diagram shown by the indicator may indicate at least a portion of the location range, based on a current location of the subject.

According to one or more exemplary embodiments, the absorbed-dose distribution diagram shown by the indicator may be updated based on a movement of the X-ray apparatus.

According to one or more exemplary embodiments, the X-ray apparatus may include a portable X-ray apparatus.

According to one or more exemplary embodiments, a method for operating a tomography apparatus may include determining a first value based on a threshold dosage of at least one X-ray allowed for a subject; generating an absorbed-dose distribution diagram that indicates a location range of the subject in which, when the at least one X-ray is irradiated to the subject based on an imaging condition, an absorbed dose of the at least one X-ray has the first value; and showing the generated absorbed-dose distribution diagram.

According to one or more exemplary embodiments, the showing of the absorbed-dose distribution diagram may include detecting the radiation shield; and updating the absorbed-dose distribution diagram based on a location of the detected radiation shield and a shielding rate of the detected radiation shield.

According to one or more exemplary embodiments, a method for operating an X-ray apparatus may include determining a first value based on a threshold dosage of at least one X-ray allowed for a subject; generating an absorbed-dose distribution diagram that indicates a location range of the subject in which, when the at least one X-ray is irradiated to the subject based on an imaging condition, an absorbed dose of the at least one X-ray has the first value; and showing the generated absorbed-dose distribution diagram.

According to one or more exemplary embodiments, the generating may include detecting a radiation shield; and updating the absorbed-dose distribution diagram based on a location of the detected radiation shield and a shielding rate of the detected radiation shield.

According to one or more exemplary embodiments, a method for showing the absorbed-dose distribution diagram may include generating an absorbed-dose distribution diagram that indicates a location range of a subject in which, when at least one X-ray is irradiated to the subject based on an X-ray imaging condition, an absorbed dose of the at least one X-ray has the first value; and showing the generated absorbed-dose distribution diagram.

According to one or more exemplary embodiments, the generating of the absorbed-dose distribution diagram may include updating the absorbed-dose distribution diagram based on the X-ray imaging condition when the imaging condition changes.

According to one or more exemplary embodiments, the generating of the absorbed-dose distribution diagram may include detecting a radiation shield; and updating the absorbed-dose distribution diagram based on a location of the detected radiation shield and a shielding rate of the detected radiation shield.

According to one or more exemplary embodiments, the imaging condition may include at least one from among the tube voltage of the at least one X-ray, the tube current of the at least one X-ray, the irradiation duration of the at least one X-ray, and the beam width of the at least one X-ray.

According to one or more exemplary embodiments, an X-ray apparatus for showing an absorbed-dose distribution diagram of at least one X-ray may include a controller configured to generate the absorbed-dose distribution diagram which indicates a location range of a subject in which, when the at least one X-ray is irradiated to the subject based on an X-ray imaging condition, an absorbed dose of the at least one X-ray of the subject has the first value; and an indicator configured to show the generated absorbed-dose distribution diagram According to one or more exemplary embodiments, the controller may be further configured to update the absorbed-dose distribution diagram based on the X-ray imaging condition when the X-ray imaging condition changes.

According to one or more exemplary embodiments, the controller may be further configured to update the absorbed-dose distribution diagram based on a location of a radiation shield that has been detected and a shielding rate of the detected radiation shield.

According to one or more exemplary embodiments, the X-ray imaging condition may include at least one from among a tube voltage of the at least one X-ray, a tube current of the at least one X-ray, an irradiation duration of the at least one X-ray, and a beam width of the at least one X-ray.

According to one or more exemplary embodiments, an X-ray system may include an X-ray radiator configured to emit at least one X-ray; a controller configured to generate an absorbed-dose distribution diagram that indicates a location range of a subject in which, when the at least one X-ray is irradiated to the subject based on an X-ray imaging condition, an absorbed dose of the at least one X-ray of the subject has the first value; and an indicator configured to show the generated absorbed-dose distribution diagram.

According to one or more exemplary embodiments, the controller may be further configured to update the absorbed-dose distribution diagram based on the X-ray imaging condition when the X-ray imaging condition changes.

According to one or more exemplary embodiments, the controller may be further configured to update the absorbed-dose distribution diagram based on a location of a radiation shield that has been detected and a shielding rate of the detected radiation shield.

According to one or more exemplary embodiments, it is possible to make a quick judgment as to whether the subject is sufficiently far away from the apparatus for capturing a medical image for safety purposes, by using the apparatus for capturing a medical image which indicates the absorbed-dose distribution diagram.

BRIEF DESCRIPTION OF THE DRAWINGS

These and/or other aspects will become apparent and more readily appreciated from the following description of several exemplary embodiments, taken in conjunction with the accompanying drawings in which.

DETAILED DESCRIPTION

Figure 1:
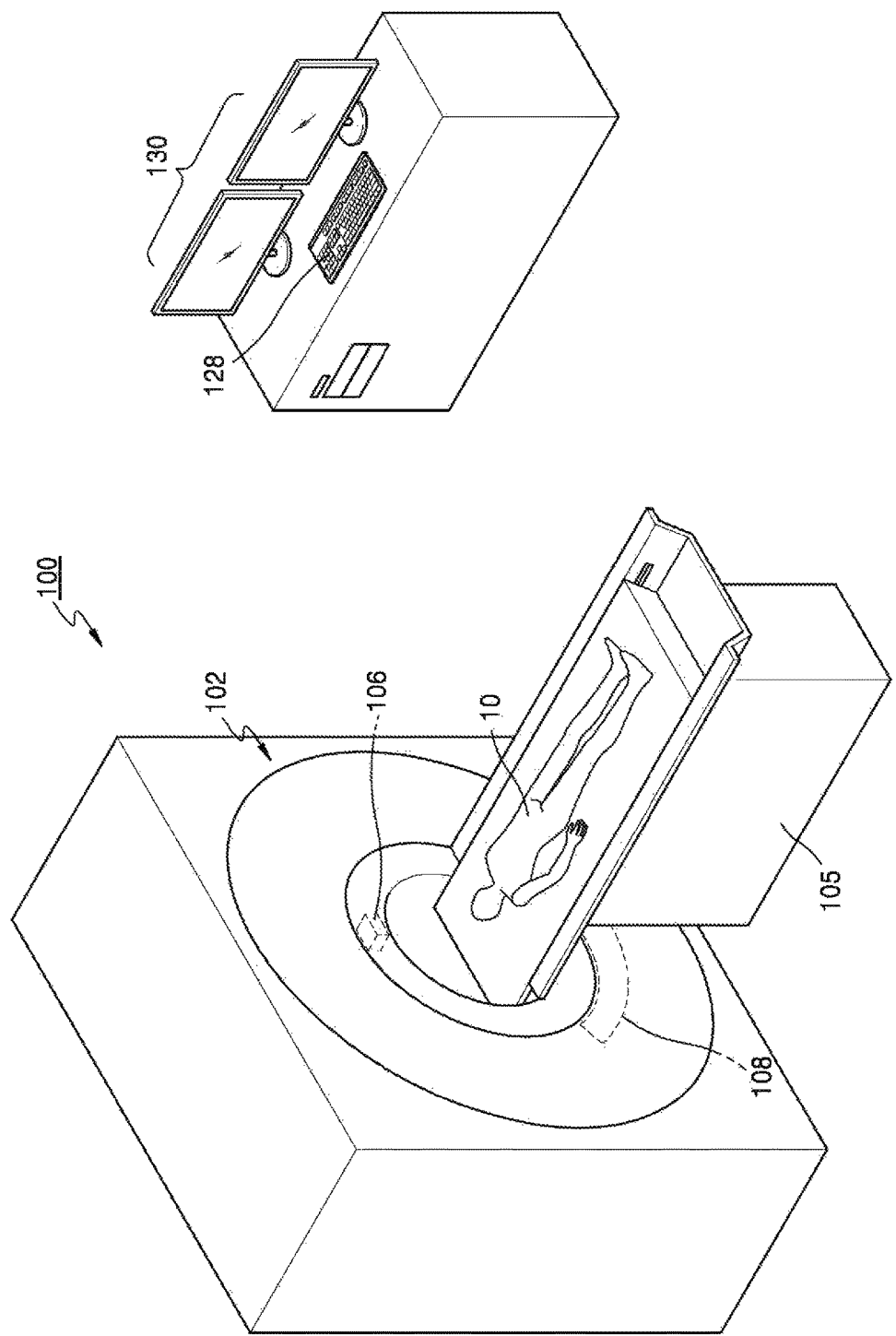
FIG. 1 schematically illustrates a computed tomography (CT) system, according to an exemplary embodiment.

Reference will now be made in detail to exemplary embodiments, examples of which are illustrated in the accompanying drawings, wherein like reference numerals refer to like elements throughout. In this regard, the present exemplary embodiments may have different forms and should not be construed as being limited to the descriptions set forth herein. Accordingly, the exemplary embodiments are merely described below, by referring to the figures, to explain aspects of the present specification.

The attached drawings for illustrating exemplary embodiments are referred to in order to gain a sufficient understanding of the present inventive concept, the merits thereof, and the objectives accomplished by the implementation of the exemplary embodiments. In this regard, the exemplary embodiments may have different forms and should not be construed as being limited to the descriptions set forth herein. Rather, these exemplary embodiments are provided so that this disclosure will be thorough and complete and will fully convey the concept of the exemplary embodiments to one of ordinary skill in the art, and the present inventive concept will only be defined by the appended claims. Like reference numerals refer to like elements throughout the specification.

Hereinafter, the terms used in the specification will be briefly defined, and the exemplary embodiments will be described in detail.

All terms including descriptive or technical terms which are used herein should be construed as having meanings that are apparent to one of ordinary skill in the art. However, the terms may have different meanings according to the intention of one of ordinary skill in the art, precedent cases, or the appearance of new technologies. Also, some terms may be arbitrarily selected by the applicant, and in this case, the meaning of the selected terms will be described in detail in the detailed description. Thus, the terms used herein have to be defined based on the meaning of the terms together with the description throughout the specification.

When a part "includes" or "comprises" an element, unless there is a particular description contrary thereto, the part can further include other elements, not excluding the other elements. Also, the term "unit" in the exemplary embodiments refers to a software component or hardware component such as a field-programmable gate array (FPGA) or an application-specific integrated circuit (ASIC), and performs a specific function. However, the term "unit" is not limited to software or hardware. The "unit" may be formed so as to be in an addressable storage medium, or may be formed so as to operate one or more processors. Thus, for example, the term "unit" may refer to components such as software components, object-oriented software components, class components, and task components, and may include processes, functions, attributes, procedures, subroutines, segments of program code, drivers, firmware, micro codes, circuits, data, a database, data structures, tables, arrays, or variables. A function provided by the components and "units" may be associated with the smaller number of components and "units", or may be divided into additional components and "units".

Reference will now be made in detail to exemplary embodiments, examples of which are illustrated in the accompanying drawings. In this regard, the exemplary embodiments may have different forms and should not be construed as being limited to the descriptions set forth herein. In the following description, well-known functions or constructions are not described in detail so as not to obscure the exemplary embodiments with unnecessary detail.

Throughout the specification, an "image" may mean multi-dimensional data formed of discrete image elements, e.g., pixels in a two-dimensional (2D) image and voxels in a three-dimensional (3D) image. For example, an image may include a medical image of an object acquired by any of an X-ray apparatus, a computed tomography (CT) apparatus, a magnetic resonance imaging (MRI) apparatus, an ultrasound diagnosis apparatus, or another medical imaging apparatus.

Throughout the specification, a "CT image" may mean an image generated by synthesizing a plurality of X-ray images that are obtained by photographing an object while a CT imaging apparatus rotates around at least one axis with respect to the object.

Throughout the specification, an "object" may include any of a human, an animal, or a portion of a human or animal. For example, the object may be an organ (e.g., the liver, heart, womb, brain, breast, or abdomen), a blood vessel, or a combination thereof. Also, the object may be a phantom. The phantom means a material having a density, an effective atomic number, and a volume that are approximately the same as those of an organism. For example, the phantom may be a spherical phantom having properties similar to the physical body.

Throughout the specification, a "user" may include, but is not limited to, a medical expert including any of a medical doctor, a nurse, a medical laboratory technologist, a medial image expert, or a technician who repairs a medical apparatus.

An X-ray apparatus is a medical imaging apparatus that acquires images of internal structures of an object by transmitting one or more X-rays, which then propagate through the human body. The X-ray apparatus may acquire medical images of an object more simply within a shorter time than other medical imaging apparatuses including an MRI apparatus and a CT apparatus. Therefore, the X-ray apparatus is widely used in simple chest photographing, simple abdomen photographing, simple skeleton photographing, simple nasal sinuses photographing, simple neck soft tissue photographing, and breast photographing.

Since a CT system is capable of providing a cross-sectional image of an object, the CT system may distinctively express an inner structure, e.g., an organ such as a kidney or a lung, of the object, as compared with a general X-ray apparatus.

The CT system may obtain a plurality of pieces of image data with a thickness of not more than 2 mm several tens to several hundred times per second, and then may process the plurality of pieces of image data, so that the CT system may provide a relatively accurate cross-sectional image of the object. According to the related art, only a horizontal cross-sectional image of the object can be obtained, but this issue has been overcome due to various image reconstruction methods. Examples of 3D image reconstruction methods are as below:

Shade surface display (SSD)—an initial 3D imaging method of displaying only voxels which have a predetermined Hounsfield Units (HU) value.

Maximum intensity projection (MIP)/minimum intensity projection (MinIP)—a 3D imaging method of displaying only voxels which have the greatest or smallest HU value from among voxels that constitute an image.

Volume rendering (VR)—an imaging method which is usable for adjusting a color and transmittance of voxels that constitute an image, according to areas of interest.

Virtual endoscopy—a method that facilitates endoscopy observation in a 3D image that is reconstructed by using the VR method or the SSD method.

Multi-planar reformation (MPR)—a method of reconstructing an image into a different cross-sectional image. A user may reconstruct an image in any desired direction.

Editing—a method of editing adjacent voxels so as to enable a user to easily observe an area of interest in volume rendering.

Voxel of interest (VOI)—a method of displaying only a selected area in volume rendering.

A CT system 100 according to an exemplary embodiment will now be described with reference to FIGS. 1 and 2. The CT system 100 may include any of various types of devices.

FIG. 1 schematically illustrates the CT system 100. Referring to FIG. 1, the CT system 100 may include a gantry 102, a table 105, and a display unit (also referred to herein as a "display device" and/or as a "display") 130.

The gantry 102 may include an X-ray generator 106 and an X-ray detector 108.

An object 10 may be positioned on the table 105.

The table 105 may move in a predetermined direction (e.g., at least one of up, down, right, and left directions) during a CT imaging procedure. In addition, the table 105 may tilt or rotate by a predetermined angle in a predetermined direction.

The gantry 102 may also tilt by a predetermined angle in a predetermined direction.

The display unit 130 may display a CT image of an object 10. In some exemplary embodiments, the display unit 130 may display a screen in order to indicate information related to CT imaging.

An input unit (also referred to herein as an "input device") 128 may receive a command which relates to operating a CT system 100 and information regarding the CT imaging from a user. The input unit 128 may include a device that is configured to receive predetermined input. In FIG. 1, the input unit 128 may be understood based on an example in which the input unit 128 includes a keyboard.

Figure 2:
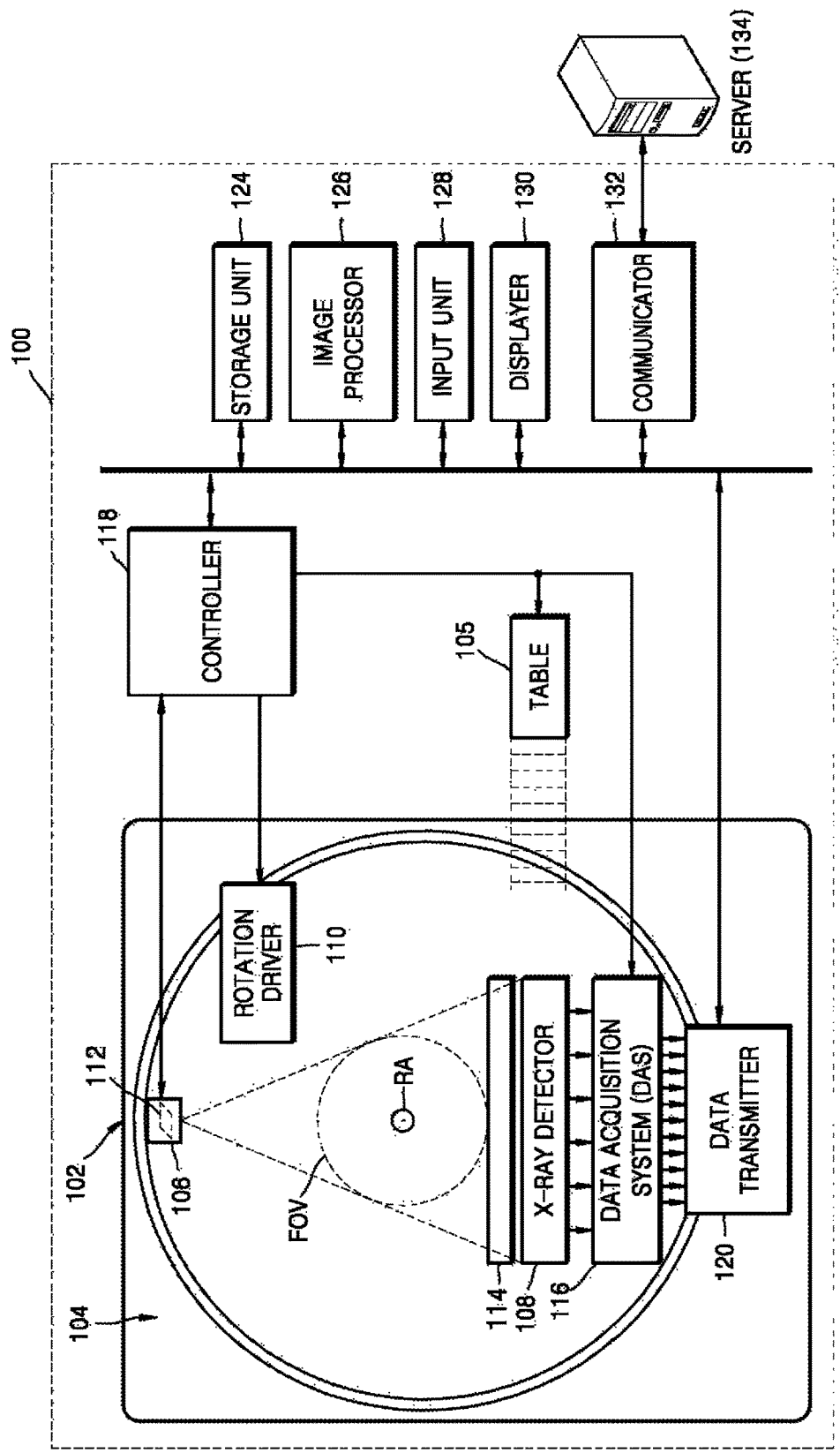
FIG. 2 is a view illustrating the structure of a CT system, according to an exemplary embodiment.

FIG. 2 is a block diagram illustrating a structure of the CT system 100.

The CT system 100 may include the gantry 102, the table 105, a control unit (also referred to herein as a "controller") 118, a storage unit (also referred to herein as a "storage device" and/or as a "storage") 124, an image processing unit (also referred to herein as an "image processor") 126, an input unit 128, a display unit 130, and a communication unit (also referred to herein as a "communicator") 132.

As described above, the object 10 may be positioned on the table 105. In the present exemplary embodiment, the table 105 may move in a predetermined direction (e.g., at least one of up, down, right, and left directions), and a movement of the table 105 may be controlled by the control unit 118.

The gantry 102 may include a rotating frame 104, the X-ray generator 106, the X-ray detecting unit 108, a rotation driving unit (also referred to herein as a "rotation driver") 110, a data acquisition system (DAS) 116, and a data transmitting unit (also referred to herein as a "data transmitter") 120.

The gantry 102 may include the rotating frame 104 which has a loop shape and which is capable of rotating with respect to a predetermined rotation axis RA. Alternatively, the rotating frame 104 may have a disc shape.

The rotating frame 104 may include the X-ray generator 106 and the X-ray detector 108 that are arranged to face each other so as to have predetermined fields of view FOV. The rotating frame 104 may also include an anti-scatter grid 114. The anti-scatter grid 114 may be positioned between the X-ray generator 106 and the X-ray detecting unit 108.

In a medical imaging system, X-ray radiation that reaches a detector (or a photosensitive film) includes not only attenuated primary radiation that forms a valuable image, but also scattered radiation that deteriorates the quality of an image. In order to transmit most of the primary radiation and to attenuate the scattered radiation, the anti-scatter grid 114 may be positioned between a patient and the detector (or the photosensitive film).

For example, the anti-scatter grid 114 may be formed by alternately stacking lead foil strips and an interspace material, such as a solid polymer material, solid polymer, or a fiber composite material. However, formation of the anti-scatter grid 114 is not limited thereto.

The rotating frame 104 may receive a driving signal from the rotation driving unit 110 and may rotate the X-ray generator 106 and the X-ray detector 108 at a predetermined rotation speed. The rotating frame 104 may receive the driving signal and power from the rotation driving unit 110 while the rotating frame 104 contacts the rotation driving unit 110 via a slip ring (not shown). Further, the rotating frame 104 may receive the driving signal and power from the rotation driving unit 110 via wireless communication.

The X-ray generator 106 may receive a voltage and current from a power distribution unit (PDU) (not shown) via a slip ring (not shown) and then a high voltage generating unit (also referred to herein as a "high voltage generator") (not shown), and may generate and emit one or more X-rays. When the high voltage generating unit applies a predetermined voltage (hereinafter, referred to as a tube voltage) to the X-ray generator 106, the X-ray generator 106 may generate X-rays having a plurality of energy spectra that correspond to the tube voltage.

The X-ray(s) generated by the X-ray generator 106 may be emitted in a predetermined form due to a collimator 112.

The X-ray detector 108 may be positioned to face the X-ray generator 106. The X-ray detector 108 may be positioned to face the X-ray generator 106. Each of the plurality of X-ray detecting devices may establish one channel, but one or more exemplary embodiments are not limited thereto.

The X-ray detecting unit 108 may detect the at least one X-ray that is generated by the X-ray generator 106 and that propagates through the object 10, and may generate an electrical signal that corresponds to an intensity of the detected X-ray.

The X-ray detector 108 may include an indirect-type X-ray detector which is configured for detecting radiation after converting the radiation into light, and a direct-type X-ray detector which is configured for detecting radiation after directly converting the radiation into electric charges. The indirect-type X-ray detector may use a scintillator. Further, the direct-type X-ray detector may use a photon counting detector. The DAS 116 may be connected to the X-ray detector 108. Electrical signals generated by the X-ray detector 108 may be acquired by the DAS 116. In addition, the electrical signals generated by the X-ray detecting unit 108 may be provided to an analog-to-digital converter (not shown) via an amplifier (not shown).

According to a slice thickness or the number of slices, only some of a plurality of pieces of data collected by the X-ray detector 108 may be provided to the image processing unit 126 via the data transmitting unit 120, or the image processing unit 126 may select only some of the plurality of pieces of data.

Such a digital signal may be provided to the image processing unit 126 via the data transmitting unit 120. The digital signal may be provided to the image processing unit 126 via a wire or wirelessly.

The control unit 118 may control an operation of each of the elements in the CT system 100. For example, the control unit 118 may control operations of the table 105, the rotation driving unit 110, the collimator 112, the DAS 116, the storage unit 124, the image processing unit 126, the input unit 128, the display unit 130, the communication unit 132, or the like.

The image processing unit 126 may receive data acquired by the DAS 116 (e.g., raw data that is data before processing), via the data transmitting unit 120, and may perform pre-processing.

The pre-processing may include, for example, a process of correcting a sensitivity irregularity between channels and/or a process of correcting signal loss due to a rapid decrease in signal strength or due to the presence of an X-ray absorbing material, such as, for example, a metal.

Data output from the image processing unit 126 may be referred to as raw data or projection data. The projection data may be stored in the storage unit 124 in condition with imaging conditions (e.g., the tube voltage, an imaging angle, etc.) which exist during the acquisition of data.

The projection data may include a group of data values that correspond to the intensity of the at least one X-ray that has passed through the object 10. For convenience of description, a group of a plurality of pieces of projection data that are simultaneously obtained from all channels at the same imaging angle is referred to as a projection data set.

The storage unit 124 may include at least one storage medium from among a flash memory-type storage medium, a hard disk-type storage medium, a multimedia card micro-type storage medium, card-type memories (e.g., an SD card, an XD memory, and the like), random access memory (RAM), static random access memory (SRAM), read-only memory (ROM), electrically erasable programmable ROM (EEPROM), programmable ROM (PROM), magnetic memory, a magnetic disc, and an optical disc.

The image processing unit 126 may be configured to reconstruct a cross-sectional image of the object 10 by using the acquired projection data set. The cross-sectional image may be a 3D image. In this aspect, the image processing unit 126 may reconstruct a 3D image of the object 10 by using a cone beam reconstruction method or the like, based on the acquired projection data set.

The input unit 128 may receive an external input with respect to any of an X-ray tomography imaging condition, an image processing condition, or the like. For example, the X-ray tomography imaging condition may include any of tube voltages, an energy value setting with respect to a plurality of X-rays, a selection of an imaging protocol, a selection of an image reconstruction method, a setting of a FOV area, the number of slices, a slice thickness, a parameter setting with respect to image post-processing, or the like. Further, the image processing condition may include any of a resolution of an image, an attenuation coefficient setting for the image, setting for an image combining ratio, or the like.

The input unit 128 may include a device that is configured for receiving a predetermined input from an external source. For example, the input unit 128 may include any one or more of a microphone, a keyboard, a mouse, a joystick, a touch pad, a touch pen, a voice recognition device, a gesture recognition device, or the like.

The display unit 130 may be configured to display an X-ray image reconstructed by the image processing unit 126.

Exchanges of data, power, or the like between the aforementioned elements may be performed by using at least one of wired communication, wireless communication, and optical communication.

The communication unit 132 may be configured to perform communication with any of an external device, an external medical apparatus, etc. via a server 134 or the like. The communication will be described below with reference to FIG. 16.

Figure 3:
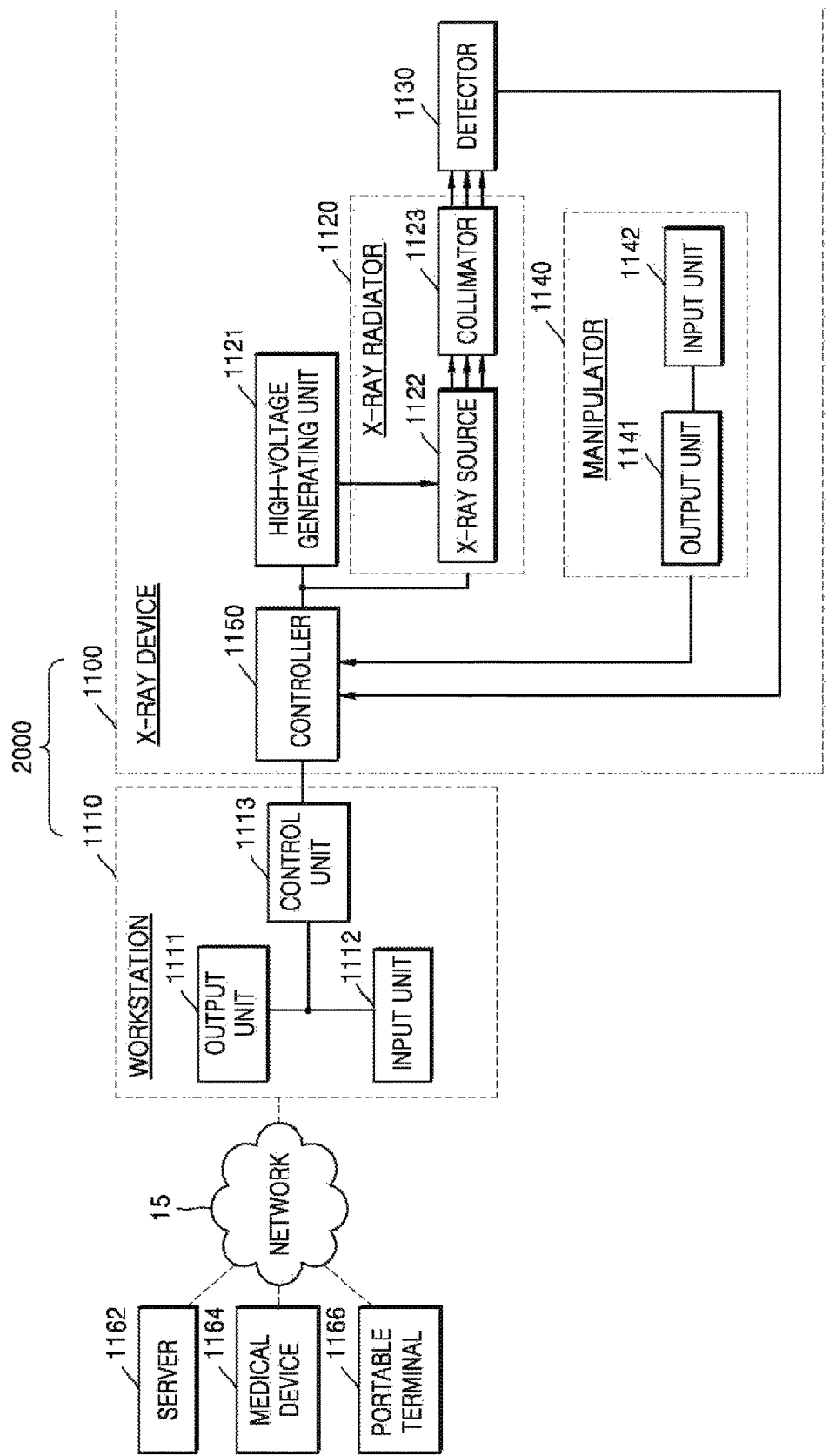
FIG. 3 is a view illustrating a configuration of an X-ray system, according to an exemplary embodiment.

FIG. 3 is a block diagram of an X-ray system 2000.

Referring to FIG. 3, the X-ray system 2000 includes an X-ray apparatus 1100 and a workstation 1110. The X-ray apparatus 1100 shown in FIG. 3 may be a fixed-type X-ray apparatus or a mobile X-ray apparatus. The X-ray apparatus 1100 may include an X-ray radiator 1120, a high voltage generator 1121, a detector 1130, a manipulator 1140, and a controller 1150. The controller 1150 may control overall operations of the X-ray apparatus 1100.

The high voltage generator 1121 generates a high voltage for generating X-rays, and applies the high voltage to an X-ray source 1122.

The X-ray radiator 1120 includes the X-ray source 1122 which is configured for receiving the high voltage from the high voltage generator 1121 in order to generate and radiate X-rays, and a collimator 1123 which is configured for guiding a path of the at least one X-ray radiated from the X-ray source 1122 and for adjusting an irradiation region which is irradiated by the at least one X-ray.

The X-ray source 1122 includes an X-ray tube that may be realized as a vacuum tube diode that includes a cathode and an anode. An inside of the X-ray tube is set as a high vacuum state of about 10 mmHg, and a filament of the anode is heated to a high temperature in order to generate thermal electrons. The filament may be a tungsten filament, and a voltage of about 10V and a current of about 3 to 5 A may be applied to an electric wire connected to the filament in order to heat the filament.

In addition, when a high voltage of about 10 kVp to about 300 kVp is applied between the cathode and the anode, the thermal electrons are accelerated to collide with a target material of the cathode, and then, an X-ray is generated. The X-ray is radiated outside via a window, and the window may be formed of a beryllium thin film. In this case, most of the energy of the electrons colliding with the target material is consumed as heat, and remaining energy is converted into one or more X-rays.

The cathode is primarily formed of copper, and the target material is disposed opposite to the anode. The target material may include a highly resistive material, such as, for example, any one or more of chromium (Cr), iron (Fe), cobalt (Co), nickel (Ni), tungsten (W), or molybdenum (Mo). The target material may be rotated by a rotating field. When the target material is rotated, an electron impact area is increased, and a heat accumulation rate per unit area may be increased by a factor of at least ten times greater than that of a case where the target material is fixed.

The voltage applied between the cathode and the anode of the X-ray tube is referred to as a tube voltage, and the tube voltage is applied from the high voltage generator 1121, and a magnitude of the tube voltage may be expressed by a crest value (kVp). When the tube voltage increases, a velocity of the thermal electrons increases, and accordingly, an energy of the at least one X-ray (energy of photon) that is generated when the thermal electrons collide with the target material is increased. The current flowing in the X-ray tube is referred to as a tube current, which may be expressed in terms of an average value (mA). When the tube current increases, the number of thermal electrons emitted from the filament is increased, and accordingly, the X-ray dose (i.e., the number of X-ray photons) generated when the thermal electrons collide with the target material is increased.

Therefore, the energy of the at least one X-ray may be adjusted according to the tube voltage, and the intensity of the at least one X-ray or the X-ray dose may be adjusted according to the tube current and the X-ray exposure time.

The detector 1130 detects an X-ray that is radiated from the X-ray radiator 1120 and has propagated through an object. The detector 1130 may be a digital detector. The detector 1130 may be implemented by using either of a thin film transistor (TFT) or a charge coupled device (CCD). Although the detector 1130 is included in the X-ray apparatus 100 in FIG. 3, the detector 1130 may be implemented as an X-ray detector that is a separate device which is capable of being connected to or separated from the X-ray apparatus 1100.

The X-ray apparatus 1100 may further include a manipulator 1140 which is configured for providing a user with an interface for manipulating the X-ray apparatus 1100. The manipulator 1140 may include an output unit (also referred to herein as an "output device" and/or as an "outputter") 1141 and an input unit (also referred to herein as an "input device" and/or as an "inputter") 1142. The input unit 1142 may receive, from a user, a command for manipulating the X-ray apparatus 1300 and various types of information related to X-ray photographing. The controller 1150 may control or manipulate the X-ray apparatus 1100 according to the information received by the input unit 1142. The output unit 1141 may output sound that represents information related to a photographing operation, such as the X-ray radiation, under the control of the controller 1150.

The workstation 1110 and the X-ray apparatus 1100 may be connected to each other via a wire or wirelessly. When they are connected to each other wirelessly, a device (not shown) which is configured for synchronizing clock signals with each other may be further included. The workstation 1110 and the X-ray apparatus 1100 may exist within physically separate spaces.

The workstation 1110 may include an output unit (also referred to herein as an "output device" and/or as an "outputter") 1111, an input unit (also referred to herein as an "input device" and/or as an "inputter") 1112, and a controller 1113. The output unit 1111 and the input unit 1112 provide a user with an interface for manipulating the workstation 1110 and the X-ray system 2000. The controller 1113 may control the workstation 1110 and the X-ray system 2000.

The X-ray apparatus 1100 may be controlled via the workstation 1110 or may be controlled by the controller 1150 included in the X-ray apparatus 1100. Accordingly, a user may control the X-ray apparatus 1100 via the workstation 1110, or may control the X-ray apparatus 1100 via the manipulator 1140 and the controller 1150 included in the X-ray apparatus 1100. In this aspect, a user may remotely control the X-ray apparatus 1100 via the workstation 1110, or may directly control the X-ray apparatus 1100.

Although the controller 1113 of the workstation 1110 is separate from the controller 1150 of the X-ray apparatus 1100 in FIG. 3, FIG. 3 is only an example. In some exemplary embodiments, the controllers 1113 and 1150 may be integrated into a single controller, and the single controller may be included in only one of the workstation 1110 and the X-ray apparatus 1100. Hereinafter, the controllers 1113 and 1150 may denote the controller 1113 of the workstation 1110 and/or the controller 1150 of the X-ray apparatus 1100.

The output unit 1111 and the input unit 1112 of the workstation 1110 may provide a user with an interface for manipulating the X-ray apparatus 1100, and the output unit 1141 and the input unit 1142 of the X-ray apparatus 1100 may also provide a user with an interface for manipulating the X-ray apparatus 100. Although the workstation 1110 and the X-ray radiation apparatus 1100 include the output units 1111 and 1141, respectively, and the input units 1112 and 1142, respectively, in FIG. 3, embodiments are not limited thereto. Only one of the workstation 1110 and the X-ray apparatus 1100 may include an output unit and/or an input unit.

Hereinafter, the input units 1112 and 1142 may denote the input unit 1112 of the workstation 1110 and/or the input unit 1142 of the X-ray apparatus 1100, and the output units 1111 and 1141 may denote the output unit 1111 of the workstation 1110 and/or the output unit 1141 of the X-ray apparatus 1100.

Examples of the input units 1112 and 1142 may include any one or more of a keyboard, a mouse, a touch screen, a voice recognizer, a fingerprint recognizer, an iris recognizer, and other input devices which are well known to one of ordinary skill in the art. The user may input a command for radiating the at least one X-ray via the input units 1112 and 1142, and the input units 1112 and 1142 may include a switch for inputting the command. The switch may be configured so that a radiation command for radiating the X-ray may be input only when the switch is pushed in two steps.

In particular, when the user pushes the switch, a prepare command for performing a pre-heating operation for X-ray radiation may be input, and in this state, when the user pushes the switch deeper, a radiation command for performing substantial X-ray radiation may be input. When the user manipulates the switch as described above, the controllers 1113 and 1150 generate signals corresponding to the commands which are input as a result of the switch manipulation, that is, a prepare signal, and transmit the generated signals to the high voltage generator 1121, which generates a high voltage for generating the X-ray(s).

When the high voltage generator 1121 receives the prepare signal from the controllers 1113 and 1150, the high voltage generator 121 starts a pre-heating operation, and when the pre-heating is finished, the high voltage generator 121 outputs a ready signal to the controllers 1113 and 1150. In addition, the detector 1130 also must prepare to detect the X-ray(s), and thus the high voltage generator 1121 performs the pre-heating operation and the controllers 1113 and 1150 transmit a prepare signal to the detector 1130 so that the detector 1130 may prepare to detect the X-ray(s) that propagate through the object. The detector 1130 prepares to detect the X-ray(s) in response to the prepare signal, and when the preparing for the detection is finished, the detector 130 outputs a ready signal to the controllers 1113 and 1150.

When the pre-heating operation of the high voltage generator 1121 is finished and the detector 1130 is ready to detect the X-ray(s), the controllers 1113 and 1150 transmit a radiation signal to the high voltage generator 1121, the high voltage generator 1121 generates and applies the high voltage to the X-ray source 1122, and the X-ray source 1122 radiates the X-ray(s).

When the controllers 1113 and 1150 transmit the radiation signal to the high voltage generator 121, the controllers 113 and 150 may transmit a sound output signal to the output units 1111 and 1141, so that the output units 1111 and 1141 output a predetermined sound and the object may recognize the radiation of the X-ray(s). The output units 1111 and 1141 may also output a sound that represents information related to photographing, in addition to the X-ray radiation. In FIG. 3, the output unit 1141 is included in the manipulator 1140; however, the exemplary embodiments are not limited thereto, and the output unit 1141 or a portion of the output unit 1141 may be located elsewhere. For example, the output unit 141 may be located on a wall of an examination room in which the X-ray photographing of the object is performed.

The controllers 1113 and 1150 control locations of the X-ray radiator 1120 and the detector 1130, photographing timing, and photographing conditions, according to photographing conditions set by the user.

In more detail, the controllers 1113 and 1150 control the high voltage generator 1121 and the detector 1130 according to the command input via the input units 1112 and 1142 so as to control radiation timing of the X-ray(s), an intensity of the X-ray(s), and a region that is irradiated by the X-ray(s). In addition, the control units 1113 and 1150 adjust the location of the detector 1130 according to a predetermined photographing condition, and control operation timing of the detector 1130.

Furthermore, the controllers 1113 and 1150 generate a medical image of the object by using image data received via the detector 1130. In detail, the controllers 1113 and 1150 may receive the image data from the detector 1130, and then generate the medical image of the object by removing noise from the image data and adjusting a dynamic range and performing interleaving of the image data.

The output units 1111 and 1141 may output the medical image generated by the controllers 1113 and 1150. The output units 1111 and 1141 may output information that is necessary for the user in order to manipulate the X-ray apparatus 1100, for example, a user interface (UI), user information, and/or object information. Examples of the output units 1111 and 1141 may include any of a speaker, a printer, a cathode ray tube (CRT) display, a liquid crystal display (LCD), a plasma display panel (PDP), an organic light emitting diode (OLED) display, a field emission display (FED), a light emitting diode (LED) display, a vacuum fluorescent display (VFD), a digital light processing (DLP) display, a flat panel display (FPD), a three-dimensional (3D) display, a transparent display, and other various output devices which are well known to one of ordinary skill in the art.

The workstation 1110 shown in FIG. 3 may further include a communicator (not shown) that may be connected to a server 1162, a medical apparatus 1164, and a portable terminal 1166 via a network 15.

The communicator may be connected to the network 15 via a wire or wirelessly in order to communicate with the server 1162, the medical apparatus 1164, and/or the portable terminal 1166. The communicator may transmit or receive data related to diagnosis of the object via the network 15, and may also transmit or receive medical images captured by the medical apparatus 1164, for example, a CT apparatus, an MRI apparatus, or an X-ray apparatus. Moreover, the communicator may receive a medical history or treatment schedule of an object (e.g., a patient) from the server 1162 in order to facilitate a diagnosis of a disease of the object. Further, the communicator may perform data communication with the portable terminal 1166, such as a mobile phone, a personal digital assistant (PDA), or a laptop computer of a medical doctor or a client, as well as the server 1162 or the medical apparatus 1164 in a hospital.

The communicator may include one or more elements configured to facilitate communication with external apparatuses. For example, the communicator may include any of a local area communication module, a wired communication module, and a wireless communication module.

The local area communication module refers to a module configured for performing local area communication with an apparatus located within a predetermined distance. Examples of local area communication technology may include, but are not limited to, a wireless local area network (LAN), Wi-Fi, Bluetooth, ZigBee, Wi-Fi Direct (WFD), ultra wideband (UWD), infrared data association (IrDA), Bluetooth low energy (BLE), and near field communication (NFC).

The wired communication module refers to a module configured for communicating by using an electric signal or an optical signal. Examples of wired communication technology may include wired communication techniques using a pair cable, a coaxial cable, and an optical fiber cable, and other wired communication techniques that are well known to one of ordinary skill in the art.

The wireless communication module transmits and/or receives a wireless signal to and/or from at least one selected from a base station, an external apparatus, and a server in a mobile communication network. In this aspect, examples of the wireless signal may include a voice call signal, a video call signal, and various types of data according to text/multimedia messages transmission.

The X-ray apparatus 1100 shown in FIG. 3 may include a plurality of digital signal processors (DSPs), an ultra-small calculator, and a processing circuit that is configured for one or more special purposes (for example, high speed analog/digital (A/D) conversion, high speed Fourier transformation, and an array process).

In addition, communication between the workstation 1110 and the X-ray apparatus 1100 may be performed using a high speed digital interface, such as low voltage differential signalling (LVDS), asynchronous serial communication, such as a universal asynchronous receiver transmitter (UART), a low latency network protocol, such as error synchronous serial communication or a controller area network (CAN), or any of other various communication methods that are well known to one of ordinary skill in the art.

Figure 4:
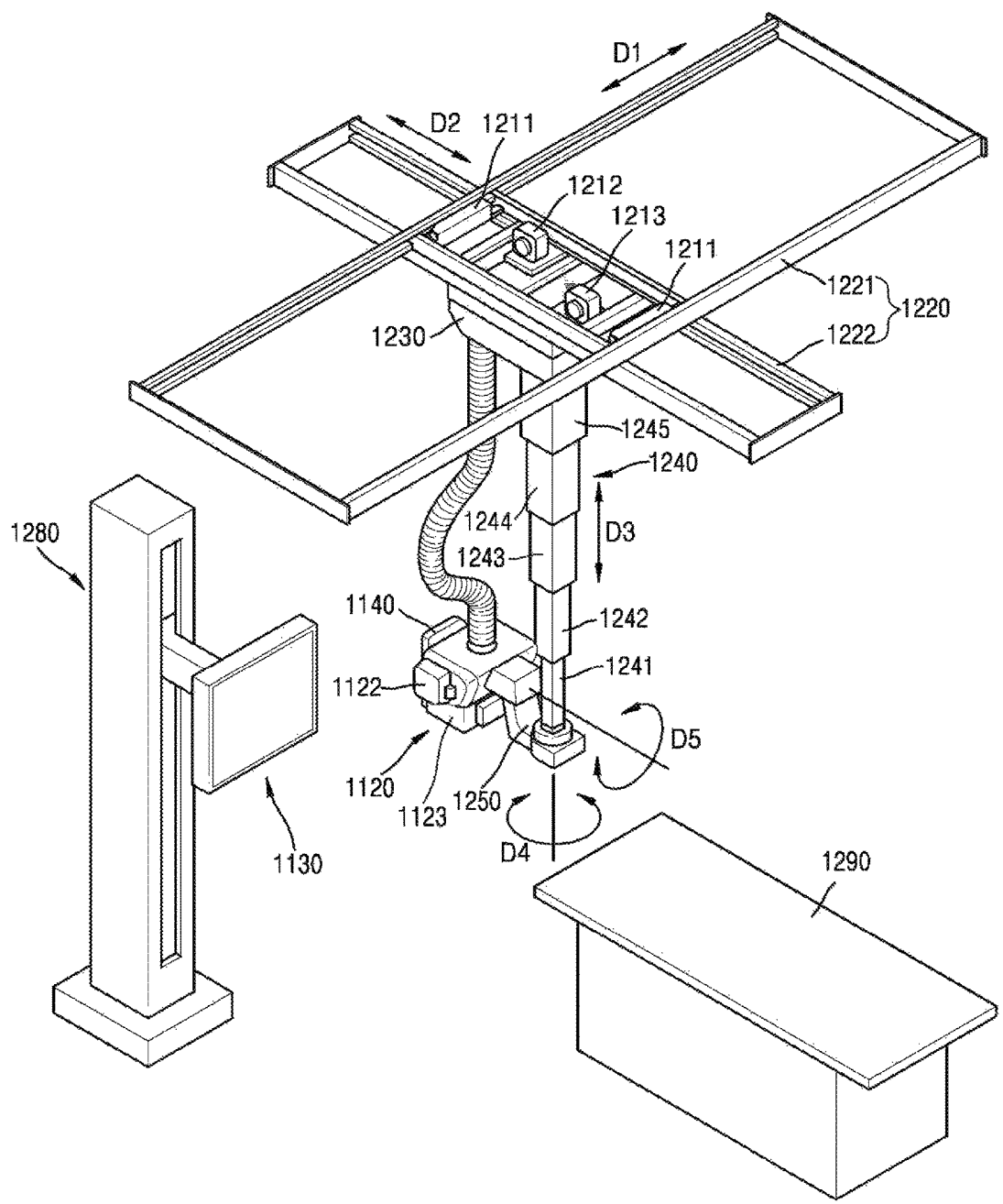
FIG. 4 is a perspective view illustrating a fixed X-ray apparatus, according to an exemplary embodiment.

FIG. 4 is a perspective view of a fixed type X-ray apparatus 1200.

The mobile X-ray apparatus 1200 may be another exemplary embodiment of the X-ray apparatus 1100 of FIG. 3. Components included in the mobile X-ray apparatus 1200 that are the same as those of the X-ray apparatus 1100 of FIG. 3 use the same reference numerals as those used in FIG. 3, and a repeated description thereof will be omitted.

Referring to FIG. 4, the fixed type X-ray apparatus 1200 includes a manipulator 1140 which is configured for providing a user with an interface for manipulating the X-ray apparatus 1200, an X-ray radiator 1120 which is configured for radiating one or more X-rays to an object, a detector 1130 which is configured for detecting at least one X-ray that has passed through the object, first, second, and third motors 1211, 1212, and 1213 which are configured for providing a driving power to transport the X-ray radiator 1120, a guide rail 1220, a moving carriage 1230, and a post frame 1240. The guide rail 220, the moving carriage 230, and the post frame 240 are formed to transport the X-ray radiator 1120 by using the driving power of the first, second, and third motors 211, 212, and 213.

The guide rail 1220 includes a first guide rail 1221 and a second guide rail 1222 that are provided to form a predetermined angle with respect to each other. The first guide rail 1221 and the second guide rail 1222 may respectively extend in directions crossing each other at 90°.

The first guide rail 1221 is provided on the ceiling of an examination room in which the X-ray apparatus 1200 is disposed.

The second guide rail 1222 is located under the first guide rail 1221, and is mounted so as to slide along the first guide rail 1221. A roller (not shown) that may move along the first guide rail 1221 may be provided on the first guide rail 1221. The second guide rail 1222 is connected to the roller in order to facilitate a movement along the first guide rail 1221.

A first direction D1 is defined as a direction in which the first guide rail 1221 extends, and a second direction D2 is defined as a direction in which the second guide rail 1222 extends. Therefore, the first direction D1 and the second direction D2 cross each other at 90°, and may be parallel to the ceiling of the examination room.

The moving carriage 1230 is disposed under the second guide rail 1222 so as to move along the second guide rail 1222. A roller (not shown) moving along the second guide rail 1222 may be provided on the moving carriage 1230.

Therefore, the moving carriage 1230 may move in the first direction D1 together with the second guide rail 1222, and may move in the second direction D2 along the second guide rail 1222.

The post frame 1240 is fixed on the moving carriage 1230 and located under the moving carriage 1230. The post frame 1240 may include a plurality of posts 1241, 1242, 1243, 1244, and 1245.

The plurality of posts 1241, 1242, 1243, 1244, and 1245 are connected to each other to be foldable, and thus, the post frame 1240 may have a length that is adjustable in a vertical direction of the examination room while in a state of being fixed to the moving carriage 1230.

A third direction D3 is defined as a direction in which the length of the post frame 1240 increases or decreases, i.e., a vertical direction. Therefore, the third direction D3 may be perpendicular to the first direction D1 and the second direction D2.

The detector 1130 detects the at least one X-ray that has passed through the object, and may be combined with a table type receptor 1290 or a stand type receptor 1280.

A rotating joint 1250 is disposed between the X-ray radiator 1120 and the post frame 1240. The rotating joint 1250 enables the X-ray radiator 1120 to be coupled to the post frame 1240, and supports a load applied to the X-ray radiator 1120.

The X-ray radiator 1120, which is connected to the rotating joint 1250, may rotate on a plane that is perpendicular to the third direction D3. In this case, a rotating direction of the X-ray radiator 1120 may be defined as a fourth direction D4.

Further, the X-ray radiator 1120 may be configured to be rotatable on a plane that is perpendicular to the ceiling of the examination room. Therefore, the X-ray radiator 1120 may rotate in a fifth direction D5 that is a rotating direction about an axis that is parallel with the first direction D1 or the second direction D2, with respect to the rotating joint 1250.

The first, second, and third motors 1211, 1212, and 1213 may be provided to respectively move the X-ray radiator 1120 in the first, second, and third directions D1, D2, and D3. The first, second, and third motors 1211, 1212, and 1213 may be electrically driven, and each of the first, second, and third motors 211, 212, and 213 may respectively include an encoder.

Each of the first, second, and third motors 1211, 1212, and 213 may be disposed at any of various locations in consideration of design convenience. For example, the first motor 1211, moving the second guide rail 1222 in the first direction D1, may be disposed around the first guide rail 1221, the second motor 1212, moving the moving carriage 230 in the second direction D2, may be disposed around the second guide rail 1222, and the third motor 1213, increasing or reducing the length of the post frame 240 in the third direction D3, may be disposed in the moving carriage 1230. In another example, the first, second, and third motors 211, 212, and 213 may be connected to a driving power transfer unit (not shown) so as to respectively linearly move the X-ray radiator 120 in the first, second, and third directions D1, D2, and D3. The driving power transfer unit may include, for example, any of a combination of a belt and a pulley, a combination of a chain and a sprocket, or a shaft, which are generally used.

In another example, motors (not shown) may be disposed between the rotating joint 1250 and the post frame 1240 and between the rotating joint 1250 and the X-ray radiator 120 in order to rotate the X-ray radiator 1120 in the fourth and fifth directions D4 and D5.

The manipulator 1140 may be disposed on a side surface of the X-ray radiator 1120.

Although FIG. 4 shows the fixed type X-ray apparatus 1200 as being connected to the ceiling of the examination room, the fixed type X-ray apparatus 1200 is merely an example for convenience of comprehension. In this aspect, X-ray apparatuses according to exemplary embodiments may include X-ray apparatuses having various structures that are well known to one of ordinary skill in the art, for example, a C-arm-type X-ray apparatus and an angiography X-ray apparatus, in addition to the fixed type X-ray apparatus 1200 of FIG. 4.

Figure 5:
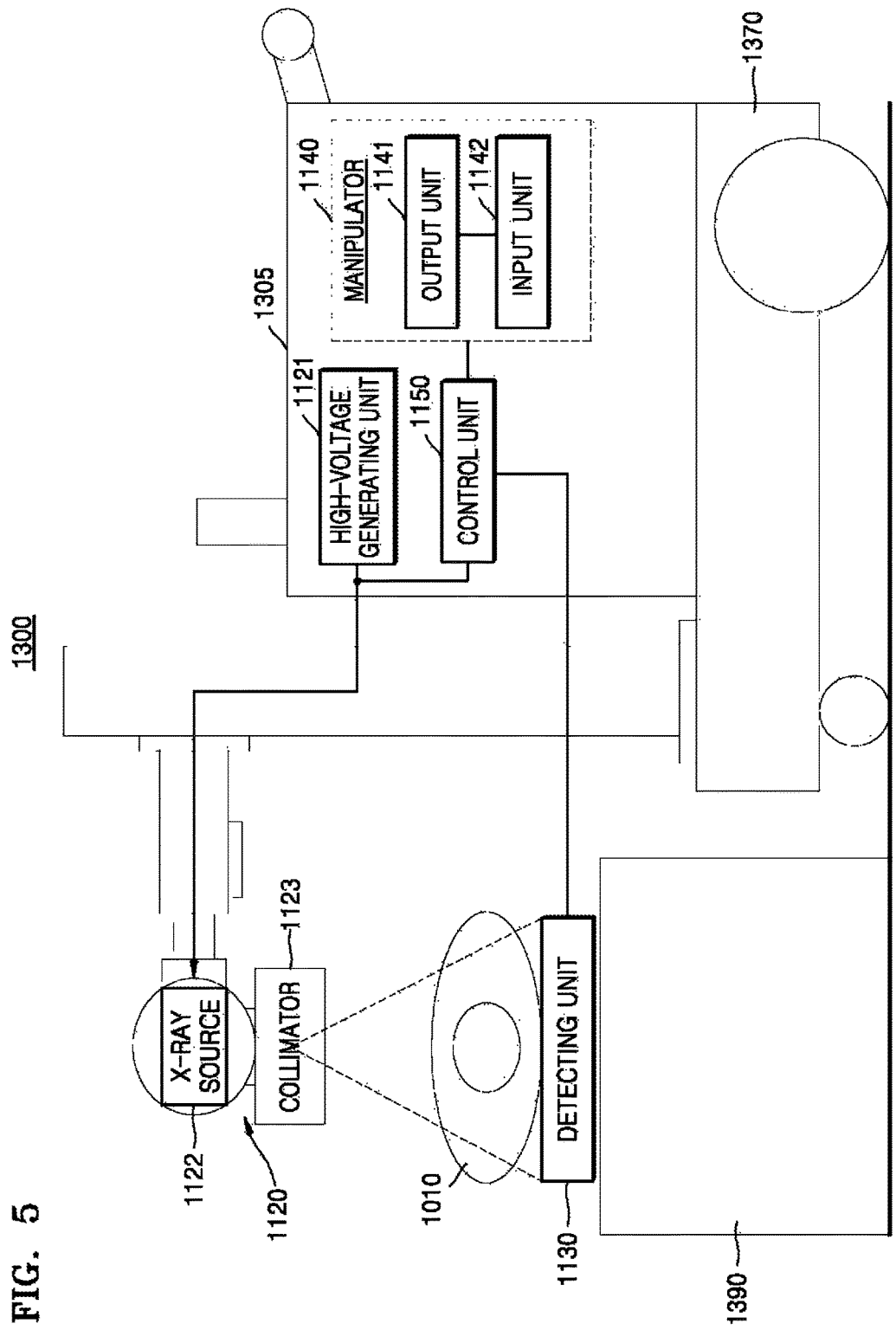
FIG. 5 is a view illustrating a portable X-ray apparatus, according to an exemplary embodiment.

FIG. 5 is a diagram showing a configuration of a mobile X-ray apparatus 1300 which is capable of performing an X-ray photographing operation regardless of a place where the photographing operation is performed.

The mobile X-ray apparatus 1300 may be another exemplary embodiment of the X-ray apparatus 1100 of FIG. 3. Components included in the mobile X-ray apparatus 1300 that are the same as those of the X-ray apparatus 1100 of FIG. 3 use the same reference numerals as those used in FIG. 3, and a repeated description thereof will be omitted.

Referring to FIG. 5, the mobile X-ray apparatus 1300 includes a transport unit 1370 which includes a wheel which is configured for transporting the mobile X-ray apparatus 1300, a main unit 1305, an X-ray radiator 1120, and a detector 1130 which is configured for detecting at least one X-ray that is radiated from the X-ray radiator 1120 toward an object and that propagates through the object. The main unit 305 includes a manipulator 1140 which is configured for providing a user with an interface for manipulating the mobile X-ray apparatus 1300, a high voltage generator 1121 which is configured for generating a high voltage applied to an X-ray source 1122, and a controller 1150 which is configured for controlling overall operations of the mobile X-ray apparatus 1300. The X-ray radiator 120 includes the X-ray source 1122 which is configured for generating the at least one X-ray, and a collimator 1123 which is configured for guiding a path along which the generated at least one X-ray is emitted from the X-ray source 1122 and for adjusting an irradiation region that is irradiated by the at least one X-ray.

The detector 1130 in FIG. 5 may not be combined with any receptor, and the detector 1130 may be a portable detector which can be situated anywhere.

In FIG. 5, the manipulator 1140 is included in the main unit 1305; however, exemplary embodiments are not limited thereto. For example, as illustrated in FIG. 4, the manipulator 1140 of the mobile X-ray apparatus 1300 may be disposed on a side surface of the X-ray radiator 1120.

Figure 6:
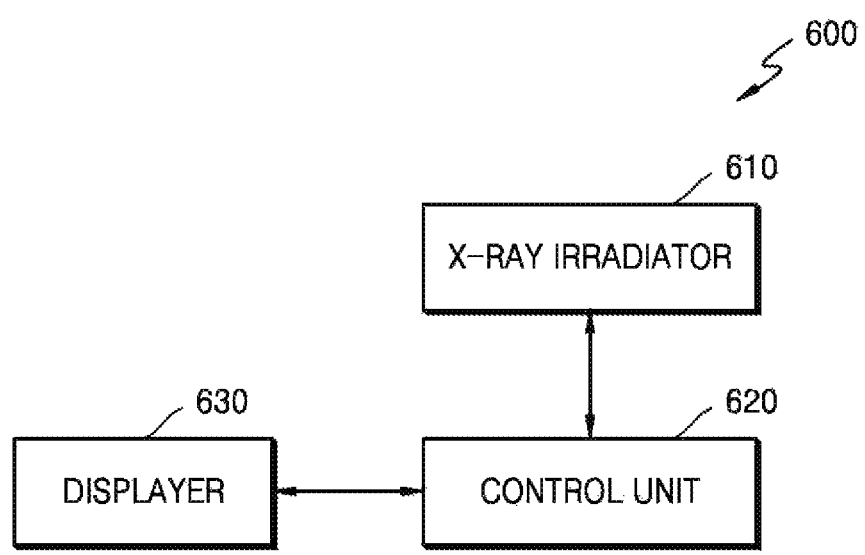
FIG. 6 is a block diagram illustrating an apparatus for capturing a medical image, according to an exemplary embodiment.

FIG. 6 is a block diagram illustrating an apparatus 600 for capturing a medical image, according to an exemplary embodiment.

The apparatus 600 shown in FIG. 6 may be an apparatus which generates a cross-sectional image of an object by causing at least one X-ray to propagate through the object. For example, the apparatus 600 may include a tomography apparatus which processes a tomography image and an X-ray apparatus which processes an X-ray image. The apparatus 600 may include, for example, at least one of a fixed tomography apparatus and a portable tomography apparatus. In some exemplary embodiments, the apparatus 600 may include a fixed X-ray apparatus and a portable X-ray apparatus.

In detail, a tomography apparatus may be an apparatus for capturing a medical image which is configured to recover a cross-sectional image after reconstructing obtained data by using radiation which has passed through the object. For example, the tomography apparatus may include a computed tomography (CT) apparatus, an optical coherence tomography (OCT), or a positron emission tomography-computed tomography (PET-CT) apparatus.

In some exemplary embodiments, an X-ray apparatus may be an apparatus for capturing a medical image which obtains an image of an interior of a human body by extracting at least one X-ray which has passed through the object. For example, the X-ray apparatus may include a digital radiography (DR) apparatus and a full-field digital mammography (FFDM).

According to an exemplary embodiment, the apparatus 600 may include at least one of an X-ray radiator (also referred to herein as an "X-ray irradiator") 610, a control unit (also referred to herein as a "controller") 620 and an indicating unit (also referred to herein as an "indicator" and/or as a "displayer") 630.

According to an exemplary embodiment, the X-ray radiator 610 may be configured to emit at least one X-ray toward the object.

In the case that the apparatus 600 is a tomography apparatus, the X-ray radiator 610 may be included in the X-ray generator 106 shown in FIGS. 1 and 2. In the case that the apparatus 600 is an X-ray apparatus, the X-ray radiator 610 may be included in the X-ray radiator 1120 shown in FIGS. 3, 4, and 5.

The at least one X-ray emitted toward the object from the X-ray radiator 610 may reach not only the object, but also the user who is near the apparatus 600 while capturing a medical image of the object. In the case that the dose of X-ray(s) which reaches the user who is near the apparatus 600 exceeds a certain limit, it may cause harm to the health of the user. In detail, in the case that the dose of X-ray(s) which exceeds a threshold dosage of X-ray(s) allowed for the user is irradiated to the user, it may affect the body of the user. Hereinafter, the user who is near the apparatus 600 will be referred to as a subject.

According to an exemplary embodiment, the X-ray radiator 610 is optional. In particular, the apparatus 600 may not include the X-ray radiator 610. The control unit 620 according to an exemplary embodiment may determine a first value based on a threshold dosage of X-ray(s) allowed for the subject.

The threshold dosage of X-ray(s) allowed for the subject means a maximum dosage of X-ray(s) within the range which does not cause harm to the body of the subject. The threshold dosage of X-ray(s) allowed for the subject may include a threshold effective dosage of X-ray(s) and a threshold equivalent dosage of X-ray(s). The threshold effective dosage of X-ray(s) may be a threshold dosage of X-ray(s) which is determined by considering the comprehensive effects of X-ray(s) on the human body when several organs of the body are irradiated. In some exemplary embodiments, a threshold equivalent dosage of X-ray(s) may be a threshold dosage of X-ray(s) which is determined by considering an average absorption dosage of X-ray(s) of tissues and organs of the body exposed to X-ray(s).

Meanwhile, the threshold dosage of X-ray(s) allowed for the subject may vary depending on whether the subject is a medical professional involved in radiology or a regular person. For example, when the subject is the medical professional involved in radiology, the threshold effective dosage of X-ray(s) is 100 mSv for the course of 5 years unless it does not exceed an annual limit of 50 mSv under the ICRP-60 recommendations. According to the ICRP-60 recommendations, the threshold effective dosage of X-ray(s) for the regular person is 1 mSv annually.

The first value, according to an exemplary embodiment, may be a value which indicates a maximum absorption dosage of X-ray(s) allowed for the subject. The absorption dose of X-ray(s) is a value which indicates absorbed energy of X-ray(s) per unit mass of an irradiated material. The first value may include the threshold effective dosage of X-ray(s) and the threshold equivalent dosage of X-ray(s) as well as the maximum absorption dosage of X-ray(s). Hereinafter, the first value is described by using an example in which the first value is the maximum absorption dosage of X-ray(s).

As described above, the first value may be determined based on the threshold dosage of X-ray(s) allowed for the subject.

The threshold dosage of X-ray(s) allowed for the subject may vary depending on whether the subject is a medical professional involved in radiology or a regular person. In this case, the first value may similarly vary depending on whether the subject is a medical professional involved in radiology or a regular person.

In some exemplary embodiments, the threshold dosage of X-ray(s) allowed for the subject may vary depending on the radiation exposure dose accumulated over the period of an imaging procedure by the subject. In this case, the first value may vary depending on the radiation exposure dose accumulated with the subject.

For example, in the case that the subject is a medical professional involved in radiology, the apparatus 600 may obtain data on the effective dose of X-ray(s) to which the subject is exposed over a year. The apparatus 600 may determine the first value based on the effective dose of X-ray(s) to which the subject is exposed over the year.

In some exemplary embodiments, the threshold dosage of X-ray(s) allowed for the subject may vary depending on whether the subject wears an appropriate shielding material. In this case, the first value may vary depending on whether the subject wears the appropriate shielding material.

The control unit 620, according to an exemplary embodiment, may be configured to generate an absorbed-dose distribution diagram which indicates a location range of the subject in which the absorbed dose of X-ray(s) of the subject has the first value, when at least one X-ray is irradiated to the subject based on imaging conditions.

According to an exemplary embodiment, the location range of the absorbed-dose distribution diagram (refer to FIG. 8) may be a curve which connects points where the absorption dose of X-ray(s) has the first value. For example, the absorbed-dose distribution diagram (refer to FIG. 8) may include a range of a circle revolving around the X-ray radiator 610.

Further, the location range of the absorbed-dose distribution diagram (refer to FIG. 9A) may vary depending on the scale of the first value. The dose of X-ray(s) irradiated per unit area is inversely proportional to the square of the distance from a location of a plane where the at least one X-ray is irradiated. Therefore, when the first value is relatively small, the absorbed-dose distribution diagram may indicate a curve at a relatively long distance from the X-ray radiator 610.

For example, a first value in the case that the subject is a medical professional involved in radiology may be greater a the first value in the case that the subject is a regular person. In this aspect, a location range of the absorbed-dose distribution diagram (refer to 905 in FIG. 9B) in the case that the subject is a regular person may have a curve at a relatively longer distance from the X-ray radiator 610 than a location range of the absorbed-dose distribution diagram (refer to 903 in FIG. 9B) in the case that the subject is a medical professional involved in radiology. In some exemplary embodiments, the first value may vary depending on whether the subject wears a shielding material. In particular, the location range of the absorbed-dose distribution diagram (refer to 901 in FIG. 9B) in the case that the subject wears a lead apron may have a curve which is marked at a location nearer to the X-ray radiator 610 than the location range of the absorbed-dose distribution diagram (refer to 903 in FIG. 9B) in the case that the subject does not wear the lead apron.

Conversely, the location range of the absorbed-dose distribution diagram (refer to FIG. 9A) may vary depending on imaging conditions. The imaging conditions, according to an exemplary embodiment, may include an imaging protocol.

For example, when disease is diagnosed by using the apparatus 600, the imaging protocol may vary depending on the type of diseases. Depending on the imaging protocol, the effective dose of X-ray(s) which is irradiated from the apparatus 600 toward the subject may change. In detail, depending on the imaging protocol, the radiation duration, the tube voltage (kvp), the tube current (mAs), or the like of an X-ray irradiated from the apparatus 600 during an X-ray imaging process is performed once may vary. In this aspect, the location range of the absorbed-dose distribution diagram may vary depending on the imaging protocol.

In some exemplary embodiments, the imaging conditions may include at least one from among the tube voltage (kvp), the tube current (mAs), the beam width, half value layer and the radiation duration of the X-ray(s).

The control unit 620, according to an exemplary embodiment, may update the absorbed-dose distribution diagram based on the variation of the imaging conditions when the imaging conditions change.

In detail, the control unit 620 may update the absorbed-dose distribution diagram as the imaging protocol changes. The control unit 620 may update the absorbed-dose distribution diagram in such a manner that the diagram would include a different location range of the same subject, as the imaging protocol changes. If at least one from among the tube voltage and the tube current increases due to the change in the imaging protocol, the control unit 620 may update the absorbed-dose distribution diagram which includes the changed location range of the subject.

In some exemplary embodiments, the control unit 620 may update the absorbed-dose distribution diagram based on the movement of the apparatus 600. The control unit 620 may adjust in such a manner that the absorbed-dose distribution diagram is changed based on the changed location of the apparatus 600.

In some exemplary embodiments, the control unit 620 may update the absorbed-dose distribution diagram in such a manner that the absorbed-dose distribution diagram indicates at least a portion of the location range of the subject, based on the current location of the subject. For example, the control unit 620 may update the absorbed-dose distribution diagram in such a manner that the absorbed-dose distribution diagram indicates only an area adjacent to the subject from within the location range, based on the current location of the subject.

In some exemplary embodiments, the control unit 620 may update the absorbed-dose distribution diagram in such a manner that the absorbed-dose distribution diagram indicates the location range in a sequential order, depending on the absorbed dose of X-ray(s). For example, the control unit 620 may update the absorbed-dose distribution diagram in such a manner that the absorbed-dose distribution diagram indicates sequentially a location range when an absorbed dose of X-ray(s) irradiated when X-ray imaging is performed once is 10 mSv, a location range when the absorbed dose is 20 mSv, and a location range when the absorbed dose is 30 mSv.

In the case that the apparatus 600 is a tomography apparatus, the control unit 620 may be included in the control unit 118 shown in FIG. 2. In the case that the apparatus 600 is an X-ray apparatus, the control unit 620 may be included in the control unit 1150 shown in FIGS. 3, 4, and 5.

The indicating unit 630, according to an exemplary embodiment, may be configured to show the absorbed-dose distribution diagram.

The indicating unit 630, according to an exemplary embodiment, may include a laser beam-radiating unit (also referred to herein as a "laser beam radiator") which is configured to indicate the absorbed-dose distribution diagram by using lasers on a plane on which the apparatus 600 is located. The plane may be the floor of the operating room in which the apparatus 600 resides. The indicating unit 630, according to an exemplary embodiment, may include a display which is wirelessly connected to the control unit, and the display may be configured to indicate the absorbed-dose distribution diagram on a screen of the display.

The indicating unit 630, according to an exemplary embodiment, may display an absorbed-dose distribution diagram which indicates location ranges of a plurality of subjects corresponding to respective first values for each of the subjects. For example, the indicating unit 630, according to an exemplary embodiment, may display an absorbed-dose distribution diagram which includes a plurality of curves (refer to 901, 903 and 905 in FIG. 9B) which indicate respective location ranges of subjects which correspond to respective first values for the subjects. The subjects, according to an exemplary embodiment, may include at least one of a medical professional involved in radiology, users wearing a lead apron and regular people.

In some exemplary embodiments, the indicating unit 630 may show the absorbed-dose distribution diagram based on the variation of imaging conditions. In detail, the indicating unit 630 may display an absorbed-dose distribution diagram which is updated as an imaging protocol changes.

In some exemplary embodiments, the indicating unit 630 may display the absorbed-dose distribution diagram which is updated based on the movement of the apparatus 600.

In some exemplary embodiments, the indicating unit 630 may display the absorbed-dose distribution diagram which indicates at least a portion of the location range of the subject, based on the current location of the subject.

In some exemplary embodiments, the indicating unit 630 may display the absorbed-dose distribution diagram based on the location of a shielding material that has been detected and the shielding rate of the detected shielding material. In the case that the apparatus 600 is a tomography apparatus, the indicating unit 630 may be included in the display unit 130 shown in FIG. 2. In the case that the apparatus 600 is an X-ray apparatus, the indicating unit 630 may be included in the displayer 1141 shown in FIGS. 3, 4, and 5.

In the case that the apparatus 600 is a tomography apparatus, the apparatus 600 may be included in the CT system 100 shown in FIGS. 1 and 2. In some exemplary embodiments, the apparatus 600 may be operable when it is connected to the CT system 100 while being included in a medical apparatus which is connected to the CT system via wired or wireless connection or a portable apparatus.

In some exemplary embodiments, in the case that the apparatus 600 is an X-ray apparatus, the apparatus 600 may be included in the X-ray apparatuses 1100, 1200 and 1300 shown in FIGS. 3, 4, and 5. In some exemplary embodiments, the apparatus 600 may be operable when it is connected to the X-ray apparatuses 1100, 1200 and 1300 while being included in a medical apparatus which is connected to the X-ray apparatuses 1100, 1200 and 1300 via wired or wireless connection or a portable apparatus.

Further, in the case that the apparatus 600 includes the control unit 620 and the indicating unit 630 according to an exemplary embodiment, the apparatus 600 may be referred to as an apparatus for displaying an absorbed-dose distribution diagram of an X-ray.

Figure 7:
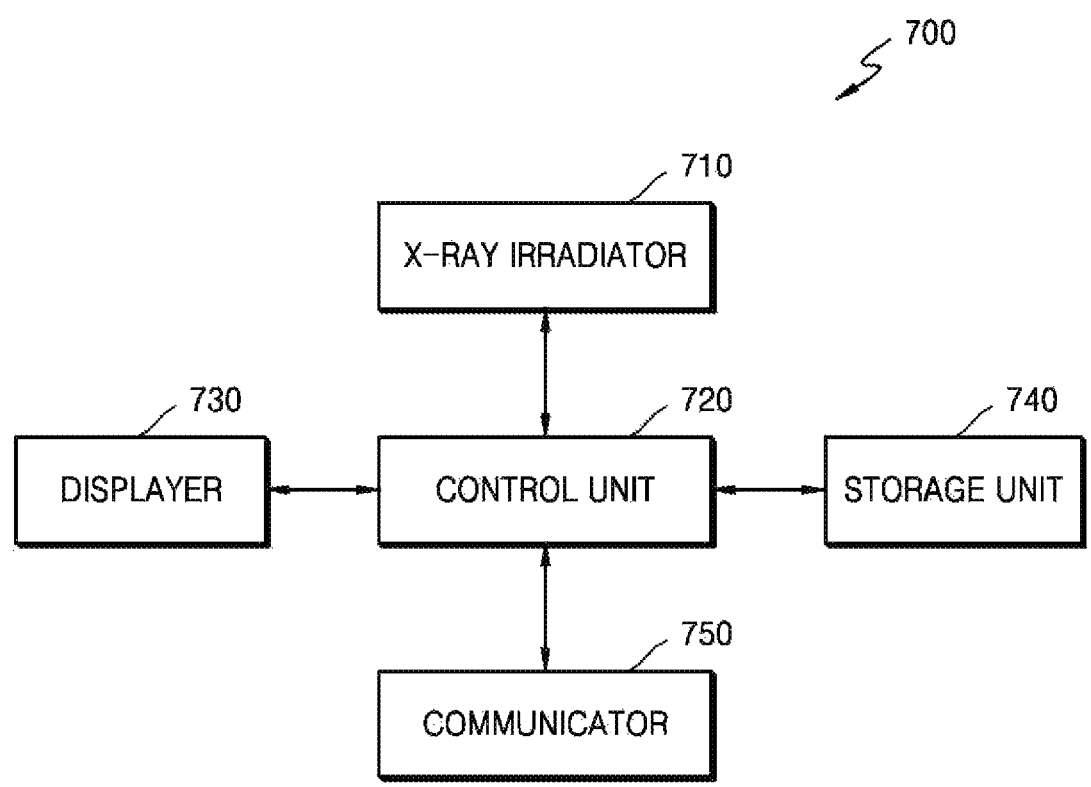
FIG. 7 is a block diagram illustrating an apparatus for capturing a medical image, according to another exemplary embodiment.

FIG. 7 is a block diagram illustrating an apparatus 700 for capturing a medical image, according to another exemplary embodiment.

The apparatus 700 shown in FIG. 7 may be an apparatus which is configured to generate a cross-sectional image of an object by causing at least one X-ray to propagate through the object. For example, the apparatus 700 may include a tomography apparatus which processes an tomography image and an X-ray apparatus which processes an X-ray image. The apparatus 700 may include, for example, at least one of a fixed tomography apparatus and a portable tomography apparatus. In some exemplary embodiments, the apparatus 700 may include the fixed X-ray apparatus and the portable X-ray apparatus.

The apparatus 700, according to an exemplary embodiment, may include at least one of an X-ray radiator 710, a control unit (also referred to herein as a "controller") 720 and an indicating unit (also referred to herein as an "indicator" and/or as a "displayer") 730. The X-ray radiator 710, the control unit 720 and the indicating unit 730 shown in FIG. 7 correspond to the X-ray radiator 610, the control unit 620 and the indicating unit 630 shown in FIG. 6. Hereinafter, repetitive explanations which are given in FIG. 6 will be omitted.

Referring to FIG. 7, the apparatus 700 may include at least one of the X-ray radiator 710, the control unit 720 and the indicating unit 730. In some exemplary embodiments, the apparatus 700 may further include at least one of a storage unit (also referred to herein as a "storage device" and/or as a "storage") 740 and a communicator 750.

The storage unit 740 may store data that relates to respective threshold dosages of X-ray(s) allowed for subjects, respective first values for the subjects and respective location ranges that correspond to the first values. In the case that the apparatus 700 is a tomography apparatus, the storage unit 740 may be included in the storage unit 124 shown in FIG. 2.

A communication unit 750 may receive, from a server (refer to 162 in FIGS. 2 and 3), data that relates to threshold dosages of X-ray(s) allowed for subjects, first values for the subjects and location ranges that correspond to the first values.

The communication unit 750 may receive data that relates to the effective dose of X-ray(s) to which a subject is exposed over a year.

In some exemplary embodiments, the communication unit 750 may receive data that relates to imaging conditions of the apparatus 700 from a server (refer to 162 in FIGS. 2 and 3). In detail, the communication unit 750 may receive data that relates to an imaging protocol from the server.

In some exemplary embodiments, the communication unit 750 may receive data that relates to a movement location and a movement pace of the apparatus 700.

In some exemplary embodiments, the communication unit 750 may receive data that relates to respective locations of the subjects relative to the apparatus 700.

In some exemplary embodiments, the communication unit 750 may wirelessly receive data that relates to the radiation shielding material from a camera attached to the subject.

In the case that the apparatus 700 is a tomography apparatus, the communication unit 750 may be included in the communication unit 126 shown in FIG. 2.

In the case that the apparatus 700 is a tomography apparatus, the apparatus 700 may be included in the CT system 100 shown in FIGS. 1 and 2. In some exemplary embodiments, the apparatus 700 may be operable when it is connected to the CT system 100 while being included in a medical apparatus which is connected to the CT system via wired or wireless connection or a portable apparatus.

Further, in the case that the apparatus 700 is the X-ray apparatus, the apparatus 700 may be included in the X-ray apparatuses 1100, 1200 and 1300 shown in FIGS. 3, 4, and 5. In some exemplary embodiments, the apparatus 700 may be operable when it is connected to the X-ray apparatuses 1100, 1200 and 1300 while being included in a medical apparatus which is connected to the X-ray apparatuses 1100, 1200 and 1300 via wired or wireless connection or a portable apparatus.

Conversely, in the case that the apparatus 700 includes the control unit 720 and the indicating unit 730 according to an exemplary embodiment, the apparatus for capturing a medical image may be referred to as an apparatus for displaying the absorbed-dose distribution diagram.

Figure 8:
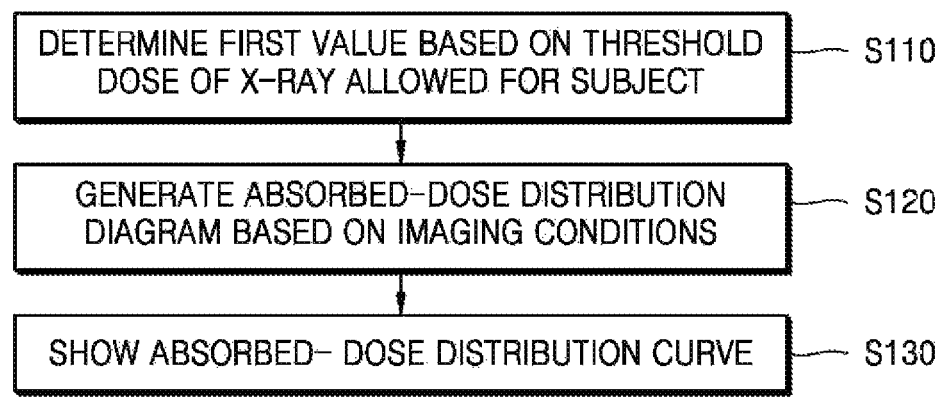
FIG. 8 is a flowchart illustrating a method for operating an apparatus for capturing a medical image, according to another exemplary embodiment.

FIG. 8 is a flowchart illustrating a method for operating the apparatuses 600 and 700, according to an exemplary embodiment.

In operation S110, the apparatuses 600 and 700 may each determine a first value based on a threshold dosage of at least one X-ray allowed for a subject.

In operation S120, the apparatuses 600 and 700 may each generate the absorbed-dose distribution diagram based on imaging conditions.

In detail, the apparatuses 600 and 700 may each generate an absorbed-dose distribution diagram which indicates a location range of the subject in which the absorbed dose of X-ray(s) of the subject has a first value, when the at least one X-ray is irradiated to the subject based on imaging conditions. The imaging conditions may include at least one from among a tube voltage (kvp), a tube current (mAs), a beam width, a half value layer, and a radiation duration of the at least one X-ray.

In operation S130, the apparatuses 600 and 700 may each display the absorbed-dose distribution diagram.

Figure 9A:
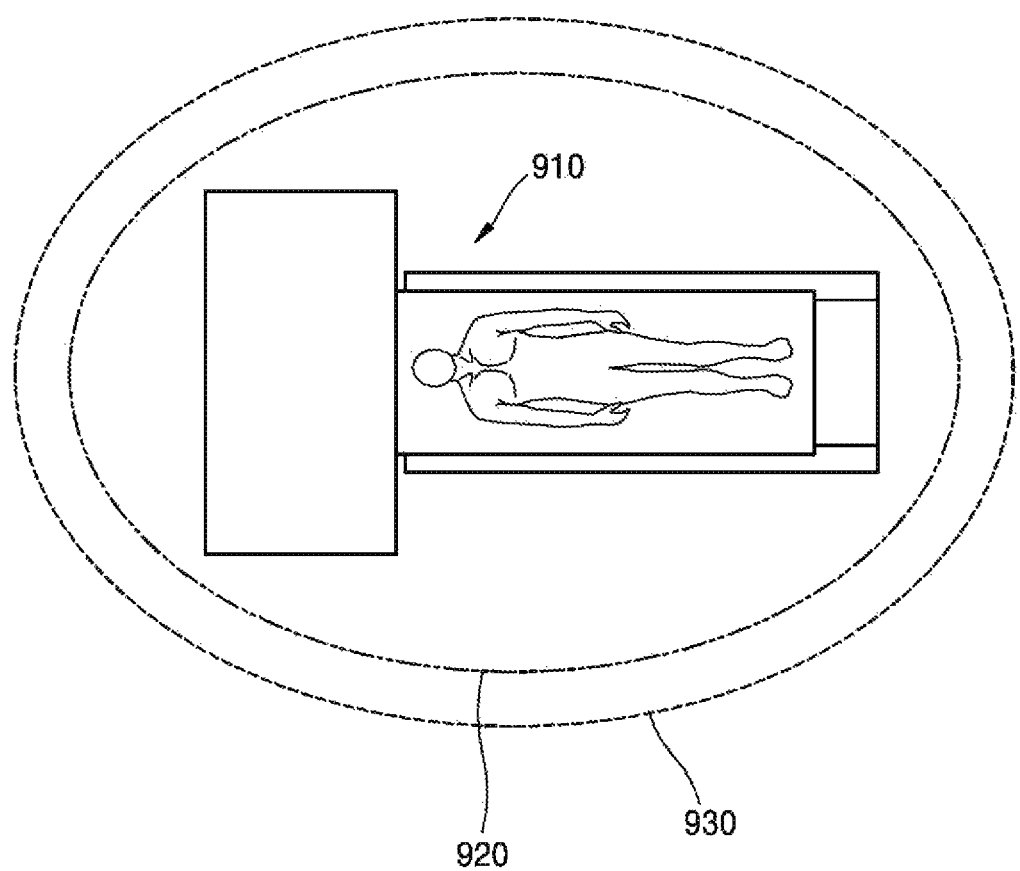
FIG. 9A is a view illustrating an apparatus for capturing a medical image, according to an exemplary embodiment.

FIG. 9A is a view illustrating the apparatuses 600 and 700, according to an exemplary embodiment.

An apparatus 910 for capturing a medical image is a view, as seen from above, of the apparatuses 600 and 700. The apparatus 910 may include a tomography apparatus and/or an X-ray apparatus.

The apparatus 910 may display an absorbed-dose distribution diagram which indicates respective location ranges of subjects which correspond to respective first values for the subjects. The subjects, for example, may include a subject who wears a lead apron and a subject who does not wear the lead apron.

For example, the absorbed-dose distribution diagram may include curves 920 and 930. The curve 920 indicates a location range of the absorbed-dose distribution diagram in the case that the subject is a medical professional involved in radiology and wears the lead apron, and the curve 930 indicates a location range 930 of the absorbed-dose distribution diagram in the case that the subject is the medical professional involved in radiology and does not wear the lead apron. The curves 920 and 930 may be indicated by different colors. In some exemplary embodiments, when the curves 920 and 930 are displayed, threshold dosages of X-ray(s) that correspond to the curves 920 and 930 may be indicated simultaneously.

The absorbed-dose distribution diagram that includes the curves 920 and 930 according to an exemplary embodiment may be displayed by a laser beam on a plane on which the apparatus 910 is located. In some exemplary embodiments, the absorbed-dose distribution diagram that includes the curves 920 and 930 may be displayed on a display unit (refer to 130 in FIG. 1) included in the apparatus 910, or on a separate display unit which is connected via a wire or wirelessly to the apparatus 910.

Meanwhile, shapes of the curves 920 and 930 may be determined by using a method as described below.

For convenience of description, it is assumed that the shapes of the curves 920 and 930 are circles, and an X-ray generator (not shown) irradiates X-rays from a single point. It is further assumed that the first value of the subject is determined based on an expected X-ray(s) exposure pattern that does not rely on possible effects of a radiation exposure dose that may have accumulated in the subject.

The first value may be determined so as to determine the shapes of the curves 920 and 930. According to an exemplary embodiment, the first value may be equivalent to a threshold effective dosage of the subject over a period of a year.

A safe location may be determined so as to determine the shapes of the curves 920 and 930.

The safe location may be determined based on an expected exposure dose of X-ray(s) of the subject over the year. The safe location may be determined as a location range that allows the expected exposure dose of X-ray(s) of the subject over the year to be the first value.

The expected exposure dose of X-ray(s) of the subject over the year may be determined based on the X-ray(s) exposure pattern of the subject. The X-ray(s) exposure pattern of the subject may account for a number of X-ray exposures per day, a number of X-ray exposures per month, and an average daily X-ray dose.

The expected exposure dose of X-ray(s) of the subject over the year may be determined based on an X-ray(s) dose reference value. The X-ray(s) dose reference value may be equal to an X-ray(s) dose value as measured at a reference location.

For example, the reference location may be located at a distance of 1 m from the X-ray generator. The X-ray(s) dose reference value may also be obtained by the apparatus 910 by measuring a dose of X-ray(s) that reaches the subject when the subject is 1 m away from the X-ray generator by using a previously determined tube voltage and a tube current of 100 mAs.

The apparatus 910 may measure the X-ray(s) dose reference value while varying the tube voltage. For example, the apparatus 910 may measure the X-ray(s) dose reference value with respect to the tube voltages of 80, 100, 120, 140, . . . (kVp).

The X-ray(s) dose reference value may be obtained by measuring a dose of X-ray(s) when a predetermined tube current and a predetermined tube voltage are used with respect to a predetermined position of the subject. The dose of X-ray(s) may be determined according to a change in the location or the tube current based on the X-ray(s) dose reference value.

More particularly, the dose of X-ray(s) may vary in an inverse proportion to a square of the distance of the subject from the X-ray generator. The dose of X-ray(s) may also vary proportionally with respect to the tube current.

An exemplary embodiment for determining the shapes of the curves 920 and 930 by using the expected exposure dose of X-ray(s) of the subject over the year will be described below.

Exemplary Embodiment 1

Exemplary Embodiment 1 relates to determining of a shape of the curve 920 when a subject does not wear a lead apron.

An expected exposure dose of X-ray(s) of the subject over a year may be first determined. The expected exposure dose of X-ray(s) of the subject over the year may be determined based on an X-ray(s) exposure pattern and the subject and an X-ray(s) dose reference value.

The expected exposure dose of X-ray(s) of the subject who is located at a distance of 1 m away from an X-ray generator over the year, i.e., the expected exposure dose of X-ray(s) over the year at 1 m, may be calculated according to Equation 1 below.

Expected exposure dose of X-ray(s) over a year at 1 m=(X-ray(s) dose reference value)λ(average daily tube current (mAs)/100 (mAs))λ(average monthly number of exposure days)×12   [Equation 1]

For example, the subject may use the tube voltage of 120 kVp and the tube current of 1000 mAs per day and may be exposed to X-ray(s) 20 times a month.

In this regard, the X-ray(s) dose reference value may also be equal to 0.05 mSv. More specifically, a dose of X-ray(s) that reaches the subject may be 0.05 mSv when the apparatus 910 uses the tube voltage of 120 kVp and the tube current of 1000 mAs, and the subject is 1 m away from the X-ray generator of the apparatus 910.

In this regard, the expected exposure dose of X-ray(s) over the year at 1 m may be calculated as 0.05 mSv×10 (1000 mAs/100 mAs)×20×12=120 mSv, according to Equation 1.

The dose of X-ray(s) varies in an inverse proportion with respect to a square of a distance between the X-ray generator and the subject, and thus a safe location a (i.e., a=a safe distance between the X-ray generator and the subject), a first value (a threshold effective dosage of the subject over a year), and the expected exposure dose of X-ray(s) over the year at 1 m may have the following relationship as expressed in Equation 2.

$1/a^2:1/(1\ m)^2$=first value:expected exposure dose of X-ray(s) over the year at 1 m   [Equation 2]

Upon summarizing Equation 2 above, the safe location a may be calculated according to Equation 3 below.

$a$=(expected exposure dose of X-ray(s) over the year at 1 m/first value)$^{1/2}$   [Equation 3]

If the threshold effective dosage of the subject, who is a medical professional involved in radiology, over the year is substituted as the expected exposure dose of X-ray(s) over the year at 1 m calculated according to Equation 1 and the first value, the safe location a may be computed as (120 mSv/50 mSv)$^{1/2}$=1.55 m according to Equation 3.

The safe location a may be expressed as a location range that allows the expected exposure dose of X-ray(s) of the subject over the year to be the first value. A range farther away from the X-ray generator than the safe location a may have an X-ray(s) exposure dose of the subject that is lower than the first value, and thus the range may be a safe location that does not cause harm to the body of the subject.

Referring to FIG. 9A, the curve 920 may connect locations which are at a distance of 1.55 m that is the safe location with respect to the X-ray generator.

Meanwhile, the safe location a may be different as between a first circumstance, i.e., when the subject is not the medical professional involved in radiology, and a second circumstance, i.e., when the subject is the medical professional involved in radiology. For example, a threshold effective dosage of the subject who is not the medical professional involved in radiology over the year may be 1 mSv. In this regard, a first value of the subject who is not the medical professional involved in radiology may be 1 mSv that is the threshold effective dosage of the subject over the year.

In this regard, when the subject is not the medical professional involved in radiology, the safe location a may be computed as $(120 \text{ mSv}/1 \text{ mSv})^{1/2} = 10.95$ m according to Equation 3.

Exemplary Embodiment 2

Exemplary Embodiment 2 relates to determining of a shape of the curve 930 when a subject wears a lead apron.

In this regard, conditions of Exemplary Embodiment 2 may be the same as those of Exemplary Embodiment 1, except that an X-ray(s) dose reference value is 0.0125 mSv. In this regard, the X-ray(s) dose reference value may be equal to ¼ of the corresponding value in Exemplary Embodiment 1.

An expected exposure dose of X-ray(s) of the subject over a year at 1 m may be calculated as 30 mSv according to Equation 1 above.

In this regard, the safe location a of the subject who is a medical professional involved in radiology may be $(30 \text{ mSv}/50 \text{ mSv})^{1/2} = 0.77$ m according to Equation 3 above.

The safe location a of the subject who is not the medical professional involved in radiology may be $(30 \text{ mSv}/1 \text{ mSv})^{1/2} = 5.48$ m according to Equation 3 above.

Figure 9B:
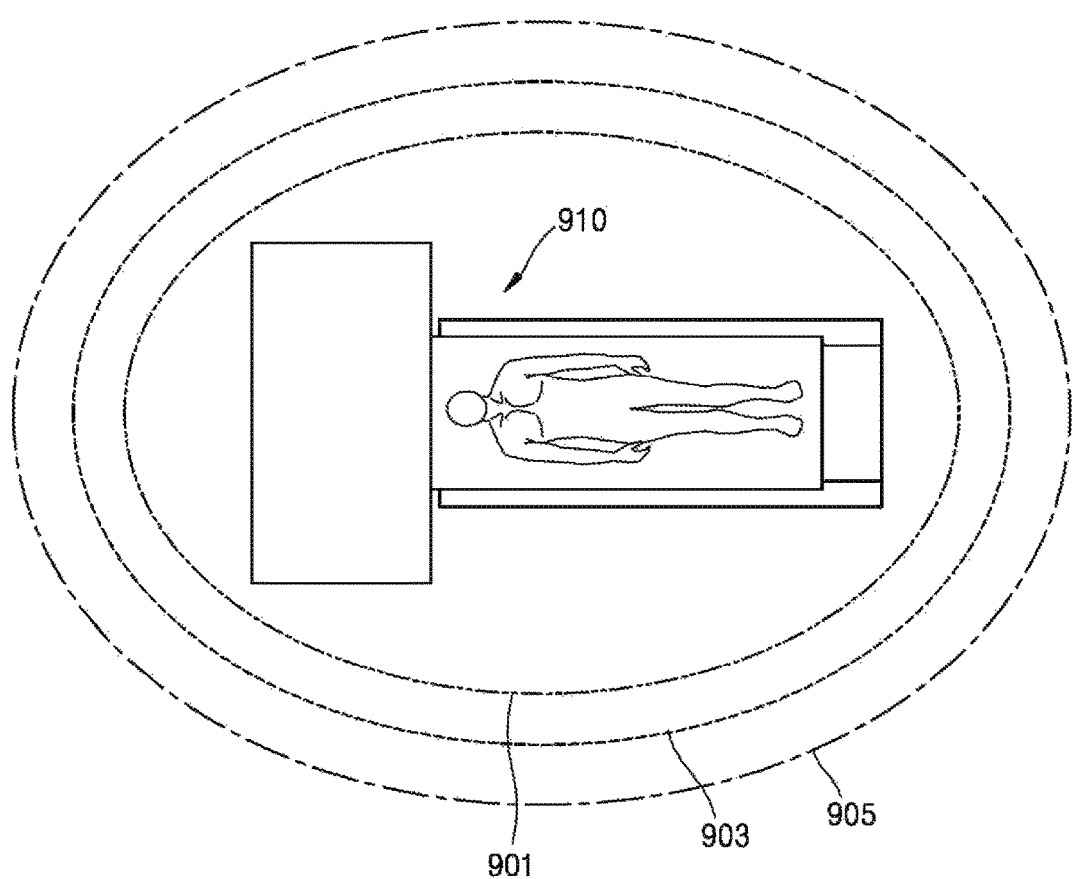
FIG. 9B is a view illustrating an apparatus for capturing a medical image, according to another exemplary embodiment.

FIG. 9B is a view illustrating the apparatuses 600 and 700, according to an exemplary embodiment.

The apparatus 910 is a view, as seen from above, of the apparatuses 600 and 700. The apparatus 910 may include a tomography apparatus and/or an X-ray apparatus.

The apparatus 910 may display an absorbed-dose distribution diagram which indicates respective location ranges of subjects which correspond to respective first values for the subjects.

For example, the absorbed-dose distribution diagram may include curves 901, 903 and 905. The curve 901 may indicate a location range of the absorbed-dose distribution diagram in the case that the subject is a medical professional involved in radiology and wears a lead apron, the curve 903 may indicate a location range of the absorbed-dose distribution diagram in the case that the subject is a medical professional involved in radiology and does not wear a lead apron, and the curve 905 may indicate a location range of the absorbed-dose distribution diagram in the case that the subject is a regular person. The curves 901, 903 and 905 may be indicated by different colors. In some exemplary embodiments, when the curves 901, 903 and 905 are displayed, threshold dosages of X-ray(s) that correspond to the curves 901, 903 and 905 may be indicated simultaneously.

The absorbed-dose distribution diagram which includes the curves 901, 903 and 905 according to an exemplary embodiment may be displayed by a laser beam on a plane on which the apparatus 910 is located. In some exemplary embodiments, the absorbed-dose distribution diagram which includes the curves 901, 903 and 905 may be displayed on a display unit (refer to 130 in FIG. 1) included in the apparatus 910, or on a separate display unit which is connected via a wire or wirelessly to the apparatus 910.

The apparatus 910 may update the absorbed-dose distribution diagram based on the variation of imaging conditions when the imaging conditions change. Accordingly, the apparatus 910 may display the absorbed-dose distribution diagram which is updated, based on the variation of the imaging conditions when the imaging conditions change.

According to an exemplary embodiment as shown in FIGS. 9A and 9B, when a user uses the apparatus 910, the user may easily recognize whether he or she remains at a safe distance with respect to the influence of X-ray radiation.

In some exemplary embodiments, according to an exemplary embodiment as shown in FIGS. 9A and 9B, it is possible for the user of the apparatus 910 to move to a safe place, based on the absorbed-dose distribution diagram which is updated, with the variation of the imaging conditions. In detail, in the case that the apparatus 910 is a portable apparatus for capturing a medical image, it is possible for the user to recognize whether he or she stays at a safe distance by using the absorbed-dose distribution diagram.

Figure 10:
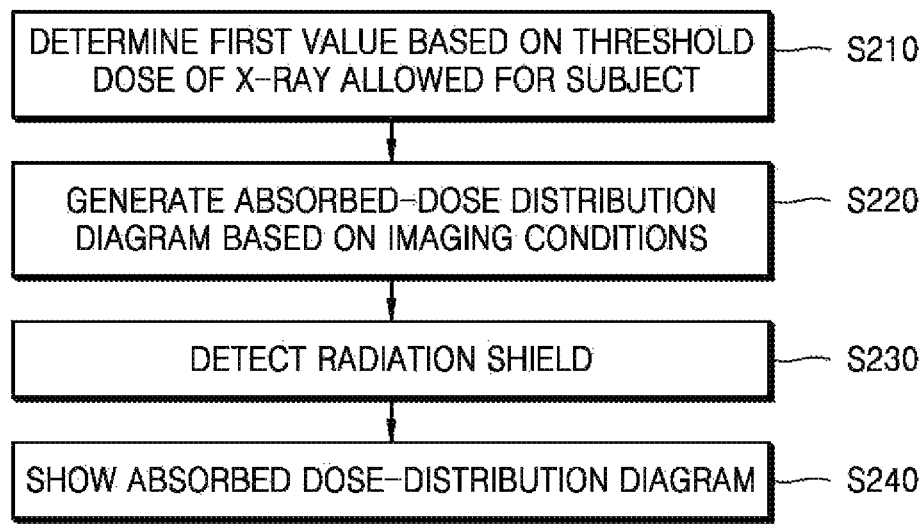
FIG. 10 is a flowchart illustrating a method for operating an apparatus for capturing a medical image, according to another exemplary embodiment.

FIG. 10 is a flowchart illustrating a method for operating the apparatuses 600 and 700, according to an exemplary embodiment.

In operation S210, the apparatuses 600 and 700 may each determine a first value based on a threshold dosage of X-ray(s) allowed for a subject.

In operation S220, the apparatuses 600 and 700 may each generate an absorbed-dose distribution diagram which indicates a location range of the subject in which an absorbed dose of X-ray of the subject has the first value, when at least one X-ray is irradiated to the subject based on imaging conditions.

In operation S230, the apparatuses 600 and 700 may each detect a radiation shield.

In operation S240, the apparatuses 600 and 700 may each display an absorbed-dose distribution diagram which is updated based on the location of the detected radiation shield and the shielding rate of the shielding material that is used in the detected radiation shield.

Figure 11:
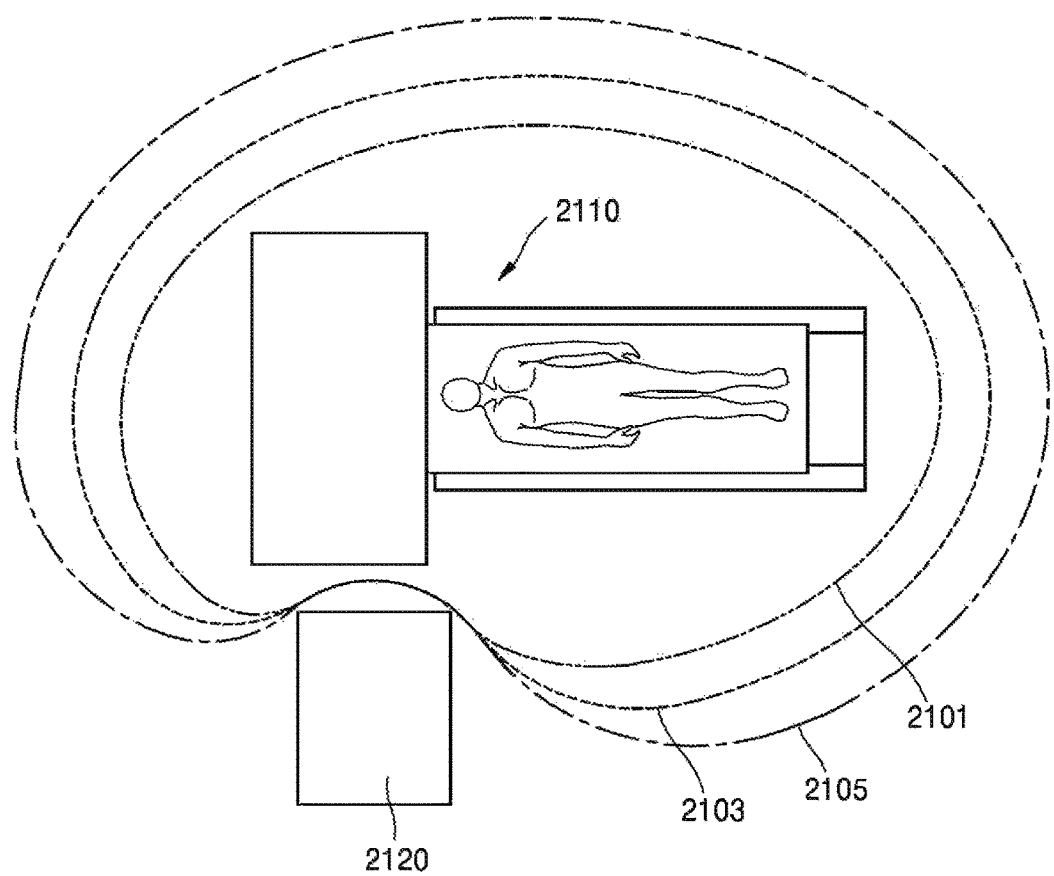
FIG. 11 is a view illustrating an apparatus for capturing a medical image, according to another exemplary embodiment.

FIG. 11 is a view illustrating the apparatuses 600 and 700, according to an exemplary embodiment.

An apparatus 2110 for capturing a medical image is a view, as seen from above, of the apparatuses 600 and 700. The apparatus 2110 may include a tomography apparatus and/or an X-ray apparatus.

The exemplary embodiment illustrated in FIG. 11 is a case in which the apparatus 2110 detects the existence of a radiation shield 2120.

The apparatus 2110 may show an absorbed-dose distribution diagram which indicates respective location ranges of subjects which correspond to respective first values for the subjects. In some exemplary embodiments, the apparatus 2110 may display the absorbed-dose distribution diagram based on the location of a detected radiation shield and the shielding rate of the detected radiation shield. According to an exemplary embodiment, the radiation shield may be detected by using a camera (not shown) attached to the subject (not shown).

In detail, the absorbed-dose distribution diagram may include at least one of curves 2101, 2103 and 2105. The curve 2101 may indicate a location range of the absorbed-dose distribution diagram in the case that the subject is a medical professional involved in radiology and wears a lead apron, the curve 2103 may indicate a location range of the absorbed-dose distribution diagram in the case that the subject is a medical professional involved in radiology and does not wear the lead apron, and the curve 2105 may indicate a location range of the absorbed-dose distribution diagram in the case that the subject is a regular person. The curves 2101, 2103 and 2105 may be indicated by different colors. In some exemplary embodiments, when the curves 2101, 2103 and 2105 are displayed, the threshold dosages of X-ray(s) that correspond to the curves 2101, 2103 and 2105 may be indicated simultaneously.

The curves 2101, 2103 and 2105 may be formed near the apparatus 910 around the area in which the radiation shield 2120 exists.

According to an exemplary embodiment as shown in FIG. 11, the user of the apparatus 2110 may easily recognize whether he/she stays safely away from the influence of X-ray radiation even when the radiation shield exists. In detail, in the case that the apparatus 2110 is a portable apparatus for capturing a medical image, it is possible for the user to recognize whether he/she stays at a safe distance by using the absorbed-dose distribution diagram, regardless of the location of the radiation shield.

Figure 12:
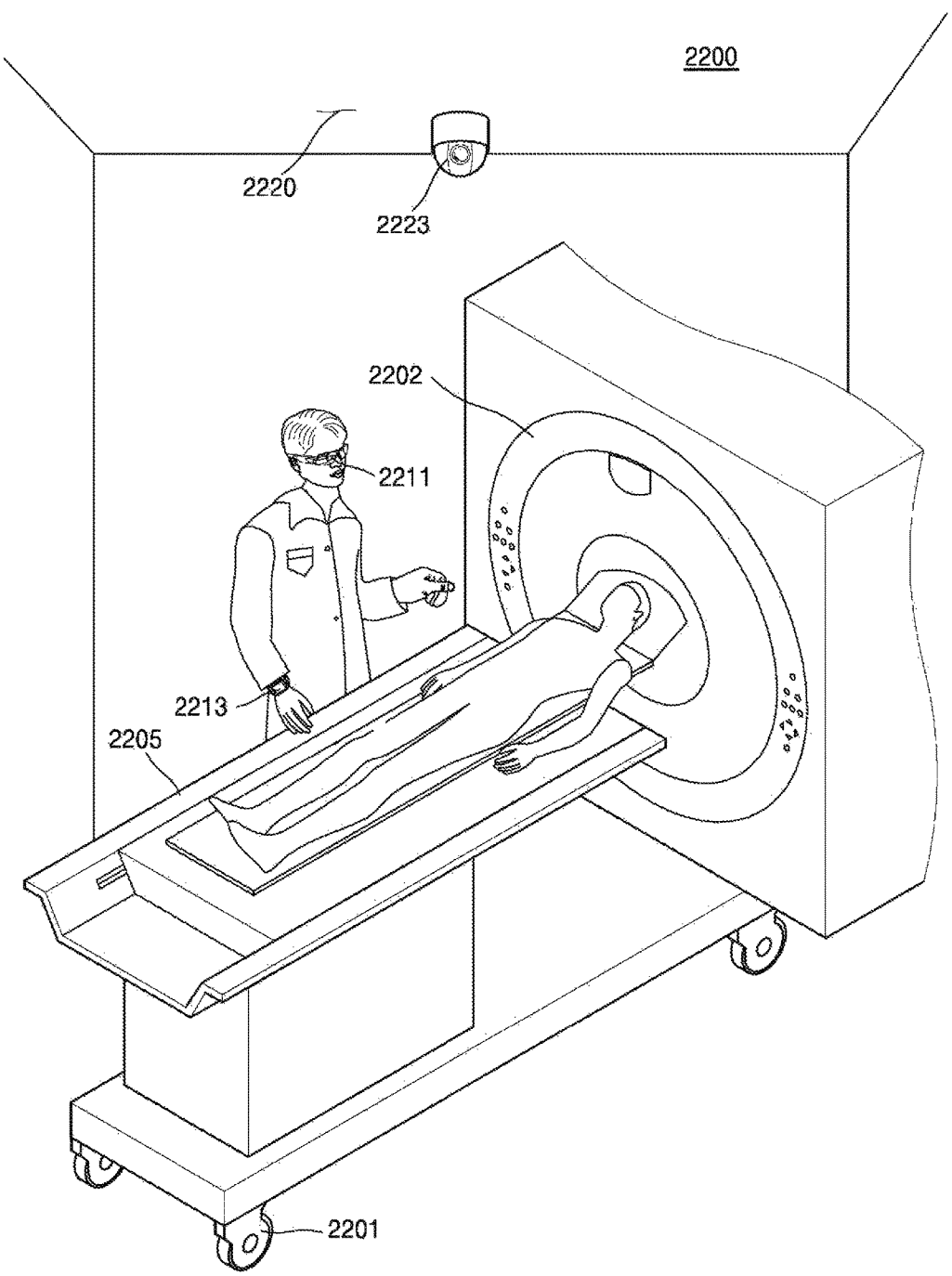
FIG. 12 is a view illustrating an apparatus for capturing a medical image, according to another exemplary embodiment.

FIG. 12 is a view illustrating an apparatus 2200 for capturing a medical image, according to an exemplary embodiment.

The apparatus 2200 shown in FIG. 12 may include a moving unit 2201 which has wheels in order to facilitate a movement of the apparatus 2200, a gantry 2202 and a table 2205. The apparatus 2200 may include the tomography apparatus and/or the X-ray apparatus. The apparatus 2200 shown in FIG. 12 is a portable tomography apparatus.

Meanwhile, the apparatus 2200 according to an exemplary embodiment may include a notifying unit (also referred to herein as a "notifier") (not shown) which sends a notification when the subject stays safely away from the X-ray radiation.

The notifying unit, according to an exemplary embodiment, may detect at least one of the location of the subject and/or the location of the shielding material by using at least one of a camera 2223 attached to a ceiling 2220 or a camera attached to the subject. For example, the camera attached to the subject may include at least one of eyeglasses 2211 and a watch 2213 worn by the subject.

The notifying unit, according to an exemplary embodiment, may send a notification when it detects a movement of the subject beyond the location range of the absorbed-dose distribution diagram. For example, in the case that the apparatus 2200 displays the absorbed-dose distribution diagram as a circle, the notifying unit may send a notification in response to detecting that the subject has moved out beyond the circle. The notifying unit may send a notification by emitting a sound. In some exemplary embodiments, the notifying unit may provide a user interface (UI) that is configured to send the user a notification. For example, the notifying unit may send a notification by using at least one of an output unit (refer to 1141 in FIG. 3), an output unit of a workstation of the X-ray system 1111 and the display unit (refer to 130 in FIG. 1) of the tomography apparatus.

Figure 13:
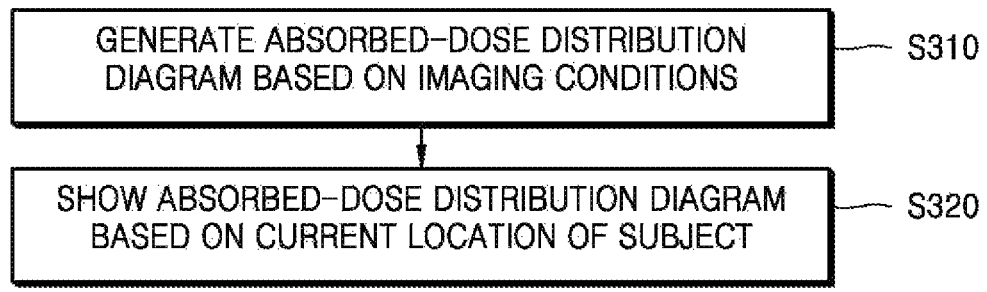
FIG. 13 is a flowchart illustrating a method for operating an apparatus for capturing a medical image which indicates an absorbed-dose distribution diagram based on a current location of a subject, according to another exemplary embodiment.

FIG. 13 is a flowchart illustrating a method for operating the apparatuses 600 and 700 which indicates an absorbed-dose distribution diagram based on the current location of the subject, according to an exemplary embodiment.

In operation S310, the apparatuses 600 and 700 may generate an absorbed-dose distribution diagram based on imaging conditions.

In detail, the apparatuses 600 and 700 may generate an absorbed-dose distribution diagram which indicates a location range of a subject in which an absorbed dose of X-ray(s) of the subject has a first value, when at least one X-ray is irradiated to the subject based on imaging conditions. The imaging conditions may include at least one from among a tube voltage (kvp), a tube current (mAs), a beam width, a half value layer and a radiation duration of X-ray(s).

In operation S320, the apparatuses 600 and 700 may each display an absorbed-dose distribution diagram which indicates at least a portion of the location range of the subject, based on the current location of the subject.

For example, the apparatuses 600 and 700 may each display the absorbed-dose distribution diagram in such a manner that it indicates only near where the subject is located within the location range of the subject. In some exemplary embodiments, the apparatuses 600 and 700 may update the absorbed-dose distribution diagram based on the movement of the subject in such a manner that it indicates only near where the subject is located within the location range of the subject.

Figure 14:
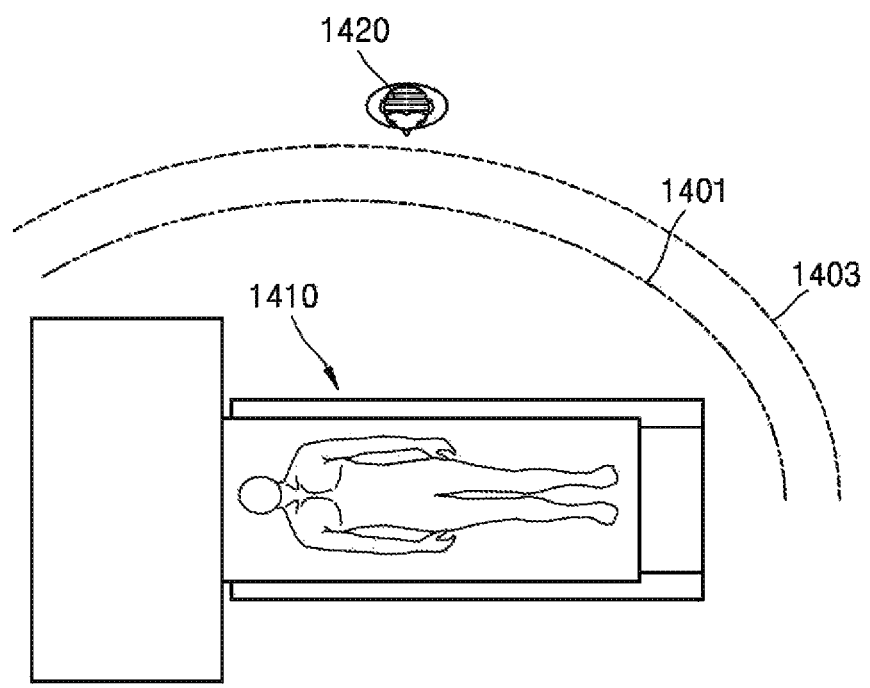
FIG. 14 is a view illustrating an apparatus for capturing a medical image which indicates an absorbed-dose distribution diagram based on a current location of a subject, according to another exemplary embodiment.

FIG. 14 is a view illustrating the apparatuses 600 and 700 displaying an absorbed-dose distribution diagram based on the location of a subject 1420, according to another exemplary embodiment.

An apparatus 1410 for capturing a medical image is a view, as seen from above, of the apparatuses 600 and 700. The apparatus 1410 may include a tomography apparatus and/or an X-ray apparatus.

The apparatus 1410 may display at least one of curves 1401 and 1403. At least one of the curves 1401 and 1403 may indicate at least a portion of the location range of the subject 1420, based on the current location of the subject 1420. The apparatus 1410 may update the absorbed-dose distribution diagram in such a manner that it indicates only near where the subject 1420 is located within the location range of the subject 1420.

Further, in the case that there are two or more subjects, the apparatus 1410 may update an absorbed-dose distribution diagram which indicates respective location ranges of the subjects based on the current location of each of the subjects.

For example, the apparatus 1410 may display the absorbed-dose distribution diagram which indicates the respective location ranges of the subjects that correspond to the respective first values for the subjects. The subjects, for example, may include a subject who wears a lead apron and a subject who does not wear the lead apron.

For example, the absorbed-dose distribution diagram may include curves 1401 and 1403. The curve 1401 may indicate a location range of the absorbed-dose distribution diagram in the case that the subject is a medical professional involved in radiology and wears the lead apron, and the curve 1403 may indicate a location range of the absorbed-dose distribution diagram in the case that the subject is a medical professional involved in radiology and does not wear the lead apron. The curves 1401 and 1403 may be indicated by different colors. In some exemplary embodiments, when the curves 1401 and 1403 are displayed, threshold dosages of X-ray(s) which correspond to the curves 1401 and 1403 may be indicated simultaneously.

The absorbed-dose distribution diagram which includes the curves 1401 and 1403 according to an exemplary embodiment may be displayed by a laser beam on a plane on which the apparatus 1410 is located. In some exemplary embodiments, the absorbed-dose distribution diagram which includes the curves 1401 and 1403 may be displayed on a display unit (refer to 130 in FIG. 1) included in the apparatus 1410, or on a separate display unit that is connected via a wire or wirelessly to the apparatus 1410.

Figure 15:
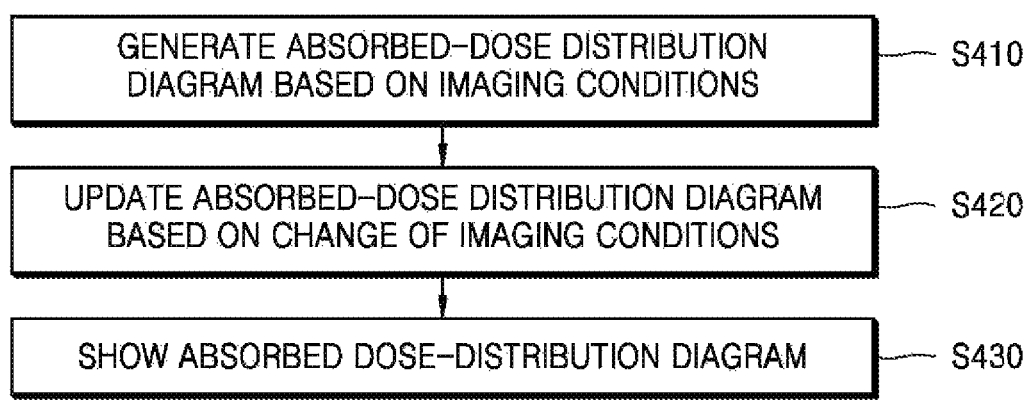
FIG. 15 is a flowchart illustrating a method for operating an apparatus for capturing a medical image which indicates an absorbed-dose distribution diagram based on a current location of a subject, according to another exemplary embodiment.

FIG. 15 is a flowchart illustrating a method for operating the apparatuses 600 and 700 displaying an absorbed-dose distribution diagram based on the variations in imaging conditions, according to an exemplary embodiment.

Hereinafter, the apparatuses 600 and 700 may each include the apparatus for displaying an absorbed-dose distribution diagram of X-ray(s) which is described in FIGS. 6 and 7.

In operation S410, the apparatuses 600 and 700 may each generate an absorbed-dose distribution diagram based on the imaging conditions.

In detail, the apparatuses 600 and 700 may each generate an absorbed-dose distribution diagram which indicates a location range of a subject in which an absorbed dose of X-ray(s) of the subject has a first value, when at least one X-ray is irradiated to the subject based on imaging conditions. For example, the imaging conditions may include at least one from among an imaging protocol, and a tube voltage (kvp), a tube current (mAs), a beam width, a half value layer, and a radiation duration of the X-ray(s).

In operation S420, the apparatuses 600 and 700 may each generate the absorbed-dose distribution diagram based on the imaging conditions.

In detail, the apparatuses 600 and 700 may each receive an input regarding the changed imaging conditions. For example, the apparatuses 600 and 700 may each receive an input regarding a changed imaging protocol or a change in the irradiation duration of the X-ray(s). The apparatuses 600 and 700 may each update the absorbed-dose distribution diagram based on the input that relates to the changed imaging conditions. If at least one of the tube voltage and the tube current increases due to the change in the imaging protocol, the apparatuses 600 and 700 may each update the absorbed-dose distribution diagram which includes the changed location range of each of the subjects.

The apparatuses 600 and 700 may not perform the operation S420 when the imaging conditions do not change. In this case, the apparatuses 600 and 700 may perform the operation S430 immediately after completing the operation S410.

In operation S430, the apparatuses 600 and 700 may each display the absorbed-dose distribution diagram.

Figure 16:
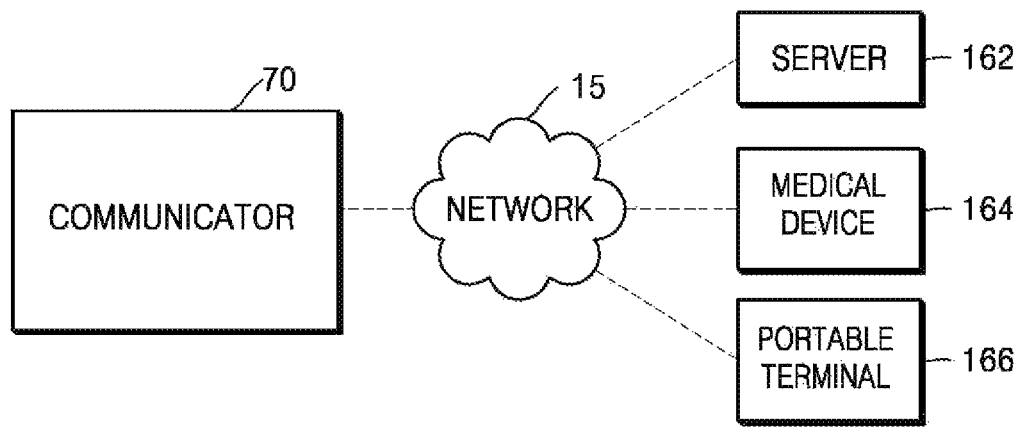
FIG. 16 is a block diagram of a communication unit.

FIG. 16 is a block diagram illustrating the communication performed by the communication unit 70.

The communication unit 70 may be wiredly or wirelessly connected to a network 15 and therefore may perform communication with any one or more of the server 162, a medical apparatus 164, and/or a portable device 166. In an exemplary embodiment, the communication unit 70 may exchange data with a hospital server or other medical apparatuses in a hospital connected via a picture archiving and communication system (PACS).

Further, the communication unit 70 may perform data communication with the portable device 166 or the like, according to the digital imaging and communications in medicine (DICOM) standard.

The communication unit 70 may transmit and receive data related to diagnosing the object 10 via the network 15. Further, the communication unit 70 may transmit and receive a medical image obtained from the medical apparatus 164 such as a magnetic resonance imaging (MRI) apparatus, an X-ray apparatus, or the like.

Furthermore, the communication unit 70 may receive a diagnosis history and/or a medical treatment schedule with respect to a patient from the server 162, and may use the diagnosis history and/or the medical treatment schedule to facilitate a diagnosis that relates to the patient. In addition, the communication unit 70 may perform data communication not only with the server 162 or the medical apparatus 164 in a hospital, but also with the portable device 166 of a user or patient.

Further, the communication unit 70 may transmit information that relates to a device error, information that relates to a quality control status, or the like to a system manager or a service manager via the network 301, and may receive a feedback regarding the information from the system manager or service manager.

Each of the apparatus 600 shown in FIG. 6 and the apparatus 700 shown in FIG. 7 may be an external medical apparatus 164 connected to a network 15 and an external and portable medical apparatus 166. In this aspect, the apparatuses 600 and 700 may be operable while being connected to the communication unit 70 shown in FIG. 16.

The above-described exemplary embodiments may be written as computer programs and may be implemented in general-use digital computers that execute the programs using a transitory or non-transitory computer-readable recording medium.

Examples of the computer-readable recording medium include magnetic storage media (e.g., read-only memory (ROM), floppy disks, hard disks, etc.), optical recording media (e.g., compact disk-read-only memory (CD-ROMs), or digital versatile disks (DVDs), etc.), and transmission media such as Internet transmission media.

While one or more exemplary embodiments have been described with reference to the figures, it will be understood by those of ordinary skill in the art that various changes in form and details may be made therein without departing from the spirit and scope of the present inventive concept as defined by the following claims.

What is claimed is:

1. A tomography apparatus comprising:
an X-ray generator configured to emit at least one X-ray;
a controller configured to determine a maximum permissible dosage of the at least one X-ray allowed for a subject, to determine a location range which causes an absorbed dose of the at least one X-ray radiated to the subject to reach the maximum permissible dosage when the subject is placed in the location range, and to generate an absorbed dose distribution diagram that indicates the location range; and
an indicator configured to show the generated absorbed-dose distribution diagram.

2. The tomography apparatus of claim 1, wherein the controller is further configured to determine the maximum permissible dosage based on occupational information of the subject, and to generate the absorbed-dose distribution diagram according to the maximum permissible dosage which is determined based on the occupational information of the subject.

3. The tomography apparatus of claim 1, wherein the indicator is configured to show, by using a laser beam, the absorbed-dose distribution diagram on a plane on which the tomography apparatus is located.

4. The tomography apparatus of claim 1, wherein the controller is further configured to determine the maximum permissible dosage based on an X-ray dosage exposed to the subject in a past one year, and to generate the absorbed-dose distribution diagram according to the maximum permissible dosage which is determined based on the X-ray dosage exposed to the subject in the past one year.

5. The tomography apparatus of claim 1, wherein the controller is further configured to determine respective maximum permissible dosages of the at least one X-ray allowed for a plurality of subjects based on respective occupational information of the plurality of subjects and respective X-ray dosages exposed to the plurality of subjects in the past one year.

6. The tomography apparatus of claim 1, wherein the controller is further configured to update the absorbed-dose distribution diagram based on an imaging condition when the imaging condition changes.

7. The tomography apparatus of claim 1, wherein the controller is further configured to generate the absorbed dose distribution diagram based on an imaging condition, and wherein the imaging condition comprises at least one from among a tube voltage of the at least one X-ray, a tube current of the at least one X-ray, an irradiation duration of the at least one X-ray, and a beam width of the at least one X-ray.

8. The tomography apparatus of claim 1, wherein the absorbed-dose distribution diagram shown by the indicator indicates at least a portion of the location range, based on a current location of the subject.

9. The tomography apparatus of claim 1, wherein the absorbed-dose distribution diagram shown by the indicator is updated based on a movement of the tomography apparatus.

10. The tomography apparatus of claim 1, wherein the tomography apparatus comprises a portable computer tomography (CT) apparatus.

11. The tomography apparatus of claim 1, wherein the absorbed-dose distribution diagram comprises a curve that indicates the location range.

12. The tomography apparatus of claim 1, wherein
the indicator comprises a display that is wirelessly connected to the controller; and
the display is configured to display the absorbed-dose distribution diagram on a screen of the display.

13. The tomography apparatus of claim 1, wherein the X-ray generator is included in a portable X-ray apparatus.

14. The tomography apparatus of claim 5, wherein the absorbed-dose distribution diagram shown by the indicator comprises a plurality of curves that indicate respective location ranges of the plurality of subjects which correspond to the respective maximum permissible dosages of the plurality of subjects.

15. The tomography apparatus of claim 14, wherein the respective maximum permissible dosages of the plurality of subjects comprise a maximum permissible dosage for a radiology technician and a maximum permissible dosage for a user who wears a lead apron.

16. A tomography apparatus comprising:
an X-ray generator configured to emit at least one X-ray;
a controller configured to determine a first value based on a threshold dosage of the at least one X-ray allowed for a subject, and to generate an absorbed-dose distribution diagram that indicates a location range of the subject in which, when the at least one X-ray is irradiated to the subject based on an imaging condition, an absorbed dose of the at least one X-ray has the first value; and
an indicator configured to show the generated absorbed-dose distribution diagram,
wherein the controller is further configured to update the absorbed-dose distribution diagram based on a location of a radiation shield that has been detected and a shielding rate of the radiation shield.

17. The tomography apparatus of claim 16, wherein the controller is further configured to receive information of the radiation shield from a camera attached to the subject.

18. A method for operating a tomography apparatus, the method comprising:
determining a maximum permissible dosage of at least one X-ray allowed for a subject;
determining a location range which causes an absorbed dose of the at least one X-ray radiated to the subject to reaches the maximum permissible dosage when the subject is placed in the location range;
generating an absorbed dose distribution diagram that indicates the location range: and
showing the generated absorbed-dose distribution diagram.

19. A method for operating a tomography apparatus, the method comprising:
determining a first value based on a threshold dosage of at least one X-ray allowed for a subject;
generating an absorbed-dose distribution diagram that indicates a location range of the subject in which, when the at least one X-ray is irradiated to the subject based on an imaging condition, an absorbed dose of the at least one X-ray has the first value; and
showing the generated absorbed-dose distribution diagram,
wherein the showing of the absorbed-dose distribution diagram comprises:
detecting a radiation shield; and
updating the absorbed-dose distribution diagram based on a location of the detected radiation shield and a shielding rate of the detected radiation shield.

20. A method for showing an absorbed-dose distribution diagram of at least one X-ray, the method comprising:
generating an absorbed-dose distribution diagram that indicates a location range of a subject in which, when the at least one X-ray is irradiated to the subject based on an X-ray imaging condition, an absorbed dose of the at least one X-ray has a first value; and
showing the generated absorbed-dose distribution diagram,
wherein the generating comprises:
detecting a radiation shield; and
updating the absorbed-dose distribution diagram based on a location of the detected radiation shield and a shielding rate of the detected radiation shield.

21. The method of claim 20, wherein the generating comprises:
updating the absorbed-dose distribution diagram based on the X-ray imaging condition when the X-ray imaging condition changes.

22. The method of claim 20, wherein the X-ray imaging condition comprises at least one from among a tube voltage of the at least one X-ray, a tube current of the at least one X-ray, an irradiation duration of the at least one X-ray, and a beam width of the at least one X-ray.

23. An apparatus for showing an absorbed-dose distribution diagram of at least one X-ray, the apparatus comprising:
a controller configured to generate the absorbed-dose distribution diagram which indicates a location range of a subject in which, when the at least one X-ray is irradiated to the subject based on an X-ray imaging condition, an absorbed dose of the at least one X-ray of the subject has a first value; and
an indicator configured to show the generated absorbed-dose distribution diagram,
wherein the controller is further configured to update the absorbed-dose distribution diagram based on a location of a radiation shield that has been detected and a shielding rate of the detected radiation shield.

24. The apparatus of claim 23, wherein the controller is further configured to update the absorbed-dose distribution diagram based on the X-ray imaging condition when the X-ray imaging condition changes.

25. The apparatus of claim 23, wherein the X-ray imaging condition comprises at least one from among a tube voltage of the at least one X-ray, a tube current of the at least one X-ray, an irradiation duration of the at least one X-ray, and a beam width of the at least one X-ray.

26. An X-ray system comprising:
- an X-ray radiator configured to emit at least one X-ray;
- a controller configured to generate an absorbed-dose distribution diagram that indicates a location range of a subject in which, when the at least one X-ray is irradiated to the subject based on an X-ray imaging condition, an absorbed dose of the at least one X-ray of the subject has a first value; and
- an indicator configured to show the generated absorbed-dose distribution diagram,
- wherein the controller is further configured to update the absorbed-dose distribution diagram based on a location of a radiation shield that has been detected and a shielding rate of the detected radiation shield.

27. The X-ray system of claim 26, wherein the controller is further configured to update the absorbed-dose distribution diagram based on the X-ray imaging condition when the X-ray imaging condition changes.

28. The X-ray system of claim 26, wherein the X-ray imaging condition comprises at least one from among a tube voltage of the at least one X-ray, a tube current of the at least one X-ray, an irradiation duration of the at least one X-ray, and a beam width of the at least one X-ray.

* * * * *